US008882902B2

(12) United States Patent
Suzuki et al.

(10) Patent No.: US 8,882,902 B2
(45) Date of Patent: Nov. 11, 2014

(54) COMPOSITE PIGMENT AND METHOD FOR PREPARATION THEREOF

(75) Inventors: Takahiro Suzuki, Kawasaki (JP); Takehiko Kasai, Kawasaki (JP)

(73) Assignee: L'Oreal, Paris (FR)

( * ) Notice: Subject to any disclaimer, the term of this patent is extended or adjusted under 35 U.S.C. 154(b) by 269 days.

(21) Appl. No.: 13/388,526

(22) PCT Filed: Aug. 4, 2009
(Under 37 CFR 1.47)

(86) PCT No.: PCT/JP2009/064084
§ 371 (c)(1),
(2), (4) Date: Jun. 14, 2012

(87) PCT Pub. No.: WO2011/016139
PCT Pub. Date: Feb. 10, 2011

(65) Prior Publication Data
US 2013/0259912 A1    Oct. 3, 2013

(51) Int. Cl.
| | | |
|---|---|---|
| *C09C 3/00* | (2006.01) | |
| *A61K 8/81* | (2006.01) | |
| *A61K 8/02* | (2006.01) | |
| *A61K 8/26* | (2006.01) | |
| *A61K 8/58* | (2006.01) | |
| *C09C 1/02* | (2006.01) | |
| *C09C 1/40* | (2006.01) | |
| *C09C 3/06* | (2006.01) | |
| *A61K 8/24* | (2006.01) | |
| *A61K 8/29* | (2006.01) | |
| *A61K 8/19* | (2006.01) | |
| *A61K 8/892* | (2006.01) | |
| *A61K 8/37* | (2006.01) | |
| *A61Q 1/06* | (2006.01) | |
| *A61Q 17/04* | (2006.01) | |
| *C09C 3/08* | (2006.01) | |
| *A61Q 1/02* | (2006.01) | |

(52) U.S. Cl.
CPC ......... *A61K 8/0233* (2013.01); *A61K 2800/614* (2013.01); *A61K 8/24* (2013.01); *A61K 8/29* (2013.01); *A61K 8/19* (2013.01); *A61K 2800/412* (2013.01); *C09C 3/006* (2013.01); *C09C 3/08* (2013.01); *C01P 2006/63* (2013.01); *A61K 2800/43* (2013.01); *A61K 2800/612* (2013.01); *A61K 8/8152* (2013.01); *C01P 2006/62* (2013.01); *C01P 2006/64* (2013.01); *A61K 8/892* (2013.01); *A61K 8/37* (2013.01); *A61K 8/0283* (2013.01); *A61K 8/26* (2013.01); *A61K 8/585* (2013.01); *A61Q 1/02* (2013.01); *C09C 1/021* (2013.01); *C01P 2004/61* (2013.01); *C09C 1/405* (2013.01); *A61Q 17/04* (2013.01); *A61Q 1/06* (2013.01); *C01P 2002/84* (2013.01); *C09C 3/063* (2013.01)

USPC ........... 106/400; 106/402; 106/414; 106/415; 106/425; 106/436; 106/461; 106/471; 106/481; 106/499; 106/600; 106/626; 106/712; 424/70.9; 424/70.12; 424/401; 424/489; 424/490; 424/502

(58) Field of Classification Search
USPC ......... 106/400, 402, 414, 415, 425, 436, 461, 106/471, 481, 499, 600, 626, 712; 424/70.9, 70.12, 401, 489, 490, 502
See application file for complete search history.

(56) References Cited

U.S. PATENT DOCUMENTS

| | | |
|---|---|---|
| 2,463,264 A | 3/1949 | Graenacher et al. |
| 4,617,390 A | 10/1986 | Hoppe et al. |
| 4,961,754 A | 10/1990 | Grollier |
| 5,166,355 A | 11/1992 | Leistner et al. |
| 5,205,837 A | 4/1993 | Andrean et al. |
| 5,237,071 A | 8/1993 | Leistner et al. |
| 5,240,975 A | 8/1993 | Winter et al. |
| 6,225,467 B1 | 5/2001 | Esteghamatian et al. |
| 6,710,091 B1 | 3/2004 | Womelsdorf et al. |
| 2003/0101908 A1* | 6/2003 | Hayashi et al. ............... 106/417 |
| 2006/0179587 A1 | 8/2006 | Brun |

FOREIGN PATENT DOCUMENTS

| | | |
|---|---|---|
| CN | 1679508 A | 10/2005 |
| CN | 1813660 A | 8/2006 |
| DE | 197 26 184 | 12/1998 |
| DE | 198 55 649 | 6/2000 |
| EP | 0 293 795 | 12/1988 |
| EP | 0 467 767 | 1/1992 |
| EP | 0 669 323 | 8/1995 |

(Continued)

OTHER PUBLICATIONS

Combined Office Action and Search Report issued Apr. 11, 2013 in Chinese Application No. 200980160823.8 (With English Translation).

Ouabbas, Y., et al., "Particle-particle coating in a cyclomix impact mixer," Powder Technology, vol. 189, No. 2, pp. 245-252, (Jan. 31, 2009).

Liang, H., et al., "UV Protection Effectiveness of Plastic Particles Coated with Titanium Dioxide by Rotational Impact Blending," Institution of Chemical Engineers, vol. 79, No. 1, pp. 49-54, (Jan. 1, 2000).

International Search Report Issued May 7, 2010 in PCT/JP09/64084 Filed Aug. 4, 2009.

*Primary Examiner* — Jane C Oswecki
(74) *Attorney, Agent, or Firm* — The Marbury Law Group, PLLC

(57) ABSTRACT

The present invention relates to a composite pigment comprising a substrate, said substrate being at least in part covered by at least one layer comprising at least one solid organic UV filter. The composite pigment can be prepared by a method comprising a step of subjecting a substrate, at least one solid organic UV filter, and optionally at least one solid inorganic UV filter, at least one additional UV filter and/or at least one coloring pigment, to a mechanochemical fusion process such as a hybridizer process. The composite pigment can be advantageously used as a component for a cosmetic composition.

20 Claims, No Drawings

(56) References Cited

FOREIGN PATENT DOCUMENTS

| | | |
|---|---|---|
| EP | 0 893 119 | 1/1999 |
| EP | 0 958 809 | 11/1999 |
| EP | 1 270 686 | 1/2003 |
| GB | 2 207 153 | 1/1989 |
| GB | 2 303 549 | 2/1997 |
| JP | 2 295912 | 12/1990 |
| JP | 6 1709 | 1/1994 |
| JP | 2003 128788 | 5/2003 |
| TW | I225470 | 12/2004 |
| WO | 93 04665 | 3/1993 |
| WO | 2004 085412 | 10/2004 |
| WO | 2006 034982 | 4/2006 |
| WO | 2006 034985 | 4/2006 |
| WO | 2006 034991 | 4/2006 |
| WO | 2006 034992 | 4/2006 |
| WO | 2006 035000 | 4/2006 |
| WO | 2006 035007 | 4/2006 |
| WO | 2009 080427 | 7/2009 |
| WO | WO2009/080427 | * 7/2009 ............... A61K 8/27 |

* cited by examiner

COMPOSITE PIGMENT AND METHOD FOR PREPARATION THEREOF

TECHNICAL FIELD

The present invention relates to a composite pigment comprising a substrate which is at least in part covered by at least one layer comprising at least one solid organic UV filter, as well as a method for preparing the composite pigment.

BACKGROUND ART

In accordance with the variety of needs in cosmetics, various research and developments have been performed for powdery components such as pigments to be used in cosmetics. In particular, for powders for cosmetics, many types of surface treatments or composite powders have been proposed. For example, JP-A-H06-1709 discloses composite pigments comprising a core particle covered by fine particles of an inorganic UV filter.

The composite pigments based on fine particles of an inorganic UV filter can provide good UV filtering effects for the UVB region (260-320 nm in wavelength). However, the UV filtering effects provided by these composite pigments based on inorganic UV filter(s) are insufficient in the UVA region (320-400 nm in wavelength).

On the other hand, composite pigments including fine particles of solid organic UV filter(s) have not yet been proposed.

Fine particles of solid organic UV filters can easily aggregate and have poor dispersibility. Therefore, it is often difficult to uniformly disperse the fine particles of solid organic UV filters in the form of primary particles in cosmetics. Therefore, the UV filtering property of the cosmetics including fine particles of solid organic UV filter(s) is difficult to be enhanced.

Further, there are some risks that fine particles of solid organic UV filter(s) may penetrate into the skin via pores on the skin, which may give adverse effects on the skin because the barrier property of the skin is not strong in pores, and that solid organic UV filter(s) when it or they irritate can easily contact with the skin, which may also give adverse effects to the skin.

DISCLOSURE OF INVENTION

Thus, an objective of the present invention is to provide a novel composite pigment which is based on solid organic UV filter(s) and can provide better UV filtering effects. In particular, the present invention aims to provide a composite pigment based on solid organic UV filter(s) with wide a UV filtering property (not only in the UVB region but also in the UVA region), and enhanced UV filtering effects.

Another objective of the present invention is to reduce the risk of fine particles of solid organic UV filter(s) penetrating into the skin via pores on the skin, and of solid organic UV filter(s) when it or they irritate easily contacting the skin to affect the skin.

The above objectives of the present invention can be achieved by a composite pigment comprising a substrate, said substrate being at least in part covered by at least one layer comprising at least one solid organic UV filter.

It is preferable that the layer comprises at least one solid inorganic UV filter. The solid inorganic UV filter may be selected from the group consisting of silicon carbide, metal oxides which may or may not be coated, and mixtures thereof.

It is possible that the layer further comprises at least one additional UV filter and/or at least one coloring pigment. The additional UV filter may be selected from the group consisting of anthranilic derivatives; dibenzoylmethane derivatives; liquid cinnamic derivatives; salicylic derivatives; camphor derivatives; benzophenone derivatives; β,β-diphenylacrylate derivatives; liquid triazine derivatives; liquid benzotriazole derivatives; benzalmalonate derivatives; benzimidazole derivatives; imidazoline derivatives; bis-benzoazolyl derivatives; p-aminobenzoic acid (PABA) and derivatives thereof; methylenebis(hydroxyphenylbenzotriazole) derivatives; benzoxazole derivatives; screening polymers and screening silicones; dimers derived from α-alkylstyrene; 4,4-diarylbutadienes; octocrylene and derivatives thereof, guaiazulene and derivatives thereof, rutin and derivatives thereof, flavonoids, biflavonoids, oryzanol and derivatives thereof, quinic acid and derivatives thereof, phenols, retinol, cysteine, aromatic amino acid, peptides having an aromatic amino acid residue, and mixtures thereof. The coloring pigment may be chosen from titanium dioxide, zirconium oxide, cerium oxide, zinc oxide, iron oxide, chromium oxide, manganese violet, ultramarine blue, chromium hydrate, ferric blue, aluminum powder, copper powder, carbon black, pigments of D&C type, lakes, pearlescent pigments, and mixtures thereof.

The substrate may have a mean diameter ranging from 0.1 μm to 30 μm. On the other hand, the above layer may have a thickness of 0.03 μm to 10 μm.

The substrate may comprise at least one inorganic material and/or at least one organic material. The inorganic material may be selected from the group consisting of mica, synthetic mica, talc, sericite, boron nitride, glass flake, calcium carbonate, barium sulfate, titanium oxide, hydroxyapatite, silica, silicate, zinc oxide, magnesium sulfate, magnesium carbonate, magnesium trisilicate, aluminum oxide, aluminum silicate, calcium silicate, calcium phosphate, magnesium oxide, bismuth oxychloride, kaolin, hydrotalcite, mineral clay, synthetic clay, iron oxide, and mixtures thereof. On the other hand, the organic material may be selected from the group consisting of poly(meth)acrylates, polyamides, silicones, polyurethanes, polyethylenes, polypropylenes, polystyrenes, polyhydroxyalkanoates, polycaprolactams, poly(butylene) succinates, polysaccharides, polypeptides, polyvinyl alcohols, polyvinyl resins, fluoropolymers, wax, amidosulfonic acid polyvalent metal salts, acylated amino acids, and mixtures thereof.

The solid organic UV filter may be selected from benzotriazole derivatives, oxanilide derivatives, triazine derivatives, triazole derivatives, vinyl-group containing amides, cinnamic acid amides, and sulfonated benzimidazoles.

The weight ratio of the substrate to the solid organic UV filter(s) may be 100:1 to 100:500.

The composite pigment according to the present invention can be prepared by a method comprising a step of subjecting a substrate, at least one solid organic UV filter, and optionally at least one solid inorganic UV filter, at least one additional UV filter and/or at least one coloring pigment, to a mechanochemical fusion process.

The composite pigment according to the present invention can be contained in a cosmetic composition.

BEST MODE FOR CARRYING OUT THE INVENTION

After diligent research, the inventors have discovered that it is possible to obtain a new composite pigment providing a wide UV filtering property (not only in the UVB region but also in the UVA region), and enhanced UV filtering effects.

The new composite pigment according to the present invention comprises a substrate which is at least in part covered by at least one layer comprising at least one solid organic UV filter. The substrate and the layer function as a core and a coating, respectively, of the composite pigment.

According to the present invention, it is possible to obtain better UV filtering effects in the UVA region by use of solid organic UV filter(s). Further, since it is possible to improve the dispersibility in cosmetics of the solid organic UV filter(s) in the form of primary particles, the UV filtering property of the cosmetics can be enhanced.

The composite pigment according to the present invention also has reduced risk of fine particles of solid organic UV filter(s) penetrating into the skin via pores on the skin and of fine particles of solid organic UV filter(s) when it or they irritate easily contacting the skin.

Since particles of solid organic UV filter(s) are firmly bonded on the substrate, the UV filter(s) cannot penetrate into the skin via pores on the skin. In addition, even if solid organic UV filter irritates, a large amount of the solid organic UV filter particles cannot directly contact with the skin, because the solid organic UV filter particles are present only on the substrate. Accordingly, the composite pigment according to the present invention is safer than an aggregate of solid organic UV filter particles.

Additionally, the composite pigment according to the present invention would also have an effect of a better feeling on use, because particles of solid organic UV filter(s) are firmly fixed on the substrate so that it is possible to reduce free solid organic UV filter particles which have a high friction coefficient such that they do not easily spread on the skin and provide an unpleasant feeling on use.

Hereafter, each of the elements constituting the composite pigment according to the present invention will be described in a detailed manner.

(Substrate)

The substrate to be used for the present invention is not limited. In other words, any substrate with any shape and/or any material can be used for the present invention.

It is preferable that the substrate is in the form of a particle with a diameter ranging from 0.1 µm to 30 µm, preferably 0.1 µm to 20 µm, and more preferably 0.1 µm to 10 µm.

It is possible to use a substrate in the form of a plate with an aspect ratio of at least 5, preferably more than 10, more preferably more than 20, and more preferably more than 50. The aspect ratio can be determined by the average thickness and the average length according to the formula: aspect ratio=length/thickness.

If the plate-like substrate is used for the present invention, it is preferable that the plate-like substrate has a length ranging from 0.3 µm to 30 µm, preferably 0.5 µm to 20 µm, more preferably 1 µm to 10 µm, and more preferably 2 µm to 5 µm.

The dimensions mentioned above are obtained by calculating the mean of the dimensions of one hundred substrates chosen on an image obtained with a scanning electron microscope.

The material of the substrate is not limited. The material can be at least one inorganic material and/or at least one organic material.

The inorganic material and/or organic material may be porous. The porosity of the material may be characterized by a specific surface area of from 0.05 $m^2/g$ to 1,500 $m^2/g$, more preferably from 0.1 $m^2/g$ to 1,000 $m^2/g$, and more preferably from 0.2 $m^2/g$ to 500 $m^2/g$ according to the BET method. However, it is preferable to use solid inorganic material(s) and/or solid organic material(s).

Preferably, the inorganic material can be selected from the group consisting of mica, synthetic mica, talc, sericite, boron nitride, glass flake, calcium carbonate, barium sulfate, titanium oxide, hydroxyapatite, silica, silicate, zinc oxide, magnesium sulfate, magnesium carbonate, magnesium trisilicate, aluminum oxide, aluminum silicate, calcium silicate, calcium phosphate, magnesium oxide, bismuth oxychloride, kaolin, hydrotalcite, mineral clay, synthetic clay, iron oxide, and mixtures thereof. In particular, natural mica, synthetic mica, sericite, kaolin, talc and mixtures thereof are preferable.

Preferably, the organic material can be selected from the group consisting of poly(meth)acrylates, polyamides, silicones, polyurethanes, polyethylenes, polypropylenes, polystyrenes, polyhydroxyalkanoates, polycaprolactams, poly (butylene) succinates, polysaccharides, polypeptides, polyvinyl alcohols, polyvinyl resins, fluoropolymers, wax, amidosulfonic acid polyvalent metal salts, acylated amino acids, and mixtures thereof. As the fluoropolymers, for example, PTFE may be used. As the amidosulfonic acid polyvalent metal salts, for example, N-lauroyltaurine calcium may be used. As the acylated amino acids, lauroyllysine may be used. In particular, polyamides such as Nylon®, polyhydroxyalkanoates such as polylactic acids, poly(meth)acrylates such as polymethylmethacrylates, silicones, and mixtures thereof are preferable.

The silicone used as the material for the substrate is not limited as long as it is in the class of organopolysiloxane. The silicone material of the substrate can be a crosslinked polysiloxane with a three-dimensional structure.

In one embodiment of the present invention, the crosslinked polysiloxane with a three-dimensional structure comprises units of formula (I): $SiO_2$, and of formula (II): $R^1SiO_{1.5}$, wherein $R^1$ comprises an organic group having a carbon atom directly connected to the silicon atom. The organic group can be chosen from a reactive organic group and an unreactive organic group. Preferably, the organic group is an unreactive organic group.

The unreactive organic group can be a $C_1$-$C_4$ alkyl group, such as a methyl, ethyl, propyl or butyl group, or a phenyl group. Preferably, the unreactive organic group is a methyl group.

The reactive organic group can be chosen from an epoxy group, a (meth)acryloyloxy group, an alkenyl group, a mercaptoalkyl group, an aminoalkyl group, a haloalkyl group, a glyceroxy group, an ureido group and a cyano group. Preferably, the reactive organic group can be chosen from an epoxy group, a (meth)acryloyloxy group, an alkenyl group, a mercaptoalkyl group and an aminoalkyl group. The reactive organic group generally comprises from 2 to 6 carbon atoms, preferably from 2 to 4 carbon atoms.

Among the epoxy groups that can be used, non-limiting mention may be made of a 2-glycidoxyethyl group, a 3-glycidoxypropyl group or a 2-(3,4-epoxycyclohexyl)propyl group.

Among the (meth)acryloyloxy groups that may be used, non-limiting mention may be made of a 3-methacryloyloxypropyl group or a 3-acryloyloxypropyl group.

Among the alkenyl groups that may be used, non-limiting mention may be made of a vinyl group, an allyl group or an isopropenyl group.

Among the mercaptoalkyl groups that may be used, non-limiting mention may be made of a mercaptopropyl group or a mercaptoethyl group.

Among the aminoalkyl groups that may be used, non-limiting mention may be made of a 3-[(2-aminoethyl)amino] propyl group, a 3-aminopropyl group or an N,N-dimethylaminopropyl group.

Among the haloalkyl groups that may be used, non-limiting mention may be made of a 3-chloropropyl group or a trifluoropropyl group.

Among the glyceroxy groups that may be used, non-limiting mention may be made of a 3-glyceroxypropyl group or a 2-glyceroxyethyl group.

Among the ureido groups that may be used, non-limiting mention may be made of a 2-ureidoethyl group.

Among the cyano groups that may be used, non-limiting mention may be made of a cyanopropyl group or a cyanoethyl group.

Preferably, in the unit of formula (II), $R^1$ denotes a methyl group.

In one embodiment of the present invention, the organosilicone material comprises the units (I) and (II) according to a unit (I)/unit (II) molar ratio ranging from 30/70 to 50/50. In a further embodiment of the present invention, the unit (I)/unit (II) ratio may range from 35/65 to 45/55.

The particles of the organosilicone material can be capable of being obtained according to a process comprising:

(a) introducing into an aqueous medium, in the presence of at least one hydrolysis catalyst and optionally of at least one surfactant, a compound (III) of formula $SiX_4$ and a compound (IV) of formula $RSiY_3$, wherein X and Y are chosen from, independently of one another, a $C_1$-$C_4$ alkoxy group, an alkoxyethoxy group including a $C_1$-$C_4$ alkoxy group, a $C_2$-$C_4$ acyloxy group, an N,N-dialkylamino group including a $C_1$-$C_4$ alkyl group, a hydroxyl group, a halogen atom and a hydrogen atom, and R is an organic group comprising a carbon atom connected directly to the silicon atom; and (b) bringing the mixture resulting from stage (a) into contact with an aqueous solution including at least one polymerization catalyst and optionally at least one surfactant, at a temperature of between 30 and 85° C.; for at least two hours.

Stage (a) corresponds to a hydrolysis reaction and stage (b) corresponds to a condensation reaction.

In stage (a), the molar ratio of the compound (III) to the compound (IV) generally ranges from 30/70 to 50/50. In one embodiment of the present invention, the molar ratio of compound (III) to compound (IV) ranges from 35/65 to 45/45. In a further embodiment of the present invention, the molar ratio of compound (III) to compound (IV) is 40/60. The ratio by weight of the water to the total weight of the compounds (III) and (IV) can range from 10/90 to 70/30. The order of introduction of the compounds (III) and (IV) generally depends on their rate of hydrolysis. The temperature of the hydrolysis reaction generally ranges from 0 to 40° C. and usually does not exceed 30° C. in order to prevent premature condensation of the compounds.

For the X and Y groups of the compounds (III) and (IV), non-limiting mention may be made of the following groups:

$C_1$-$C_4$ alkoxy groups such as the methoxy or ethoxy groups; alkoxyethoxy groups including a $C_1$-$C_4$ alkoxy group, such as the methoxyethoxy or butoxyethoxy groups; $C_2$-$C_4$ acyloxy groups such as the acetoxy or propionyloxy groups; N,N-dialkylamino groups including a $C_1$-$C_4$ alkyl group, such as the dimethylamino or diethylamino groups; and halogen atoms such as the chlorine or bromine atoms.

Among the compounds of formula (III) that may be used according to the present disclosure, non-limiting mention may be made of tetramethoxysilane, tetraethoxysilane, tetrabutoxysilane, trimethoxyethoxysilane, tributoxyethoxysilane, tetraacetoxysilane, tetrapropioxysilane, tetra(dimethylamino)silane, tetra(diethylamino)silane, silanetetraol, chlorosilanetriol, dichlorodisilanol, tetrachlorosilane or chlorotrihydrosilane. In one embodiment of the present invention, the compound of formula (III) is chosen from tetramethoxysilane, tetraethoxysilane, and tetrabutoxysilane, and mixtures thereof.

The compound of formula (III) results, after the polymerization reaction, in the formation of the units of formula (I).

The compound of formula (IV) results, after the polymerization reaction, in the formation of the units of formula (II).

The R group in the compound of formula (IV) has the meaning as described for the $R^1$ group for the compound of formula (II).

Among examples of compounds of formula (IV) comprising an unreactive organic group R, non-limiting mention may be made of methyltrimethoxysilane, ethyltriethoxysilane, propyltributoxysilane, butyltributoxysilane, phenyltrimethoxyethoxysilane, methyltributoxyethoxysilane, methyltriacetoxysilane, methyltripropioxysilane, methyltri(dimethylamino)silane, methyltri(diethylamino)silane, methylsilanetriol, methylchlorodisilanol, methyltrichlorosilane or methyltrihydrosilane.

As examples of compounds of formula (IV) comprising a reactive organic group R, non-limiting mention may be made of: silanes having an epoxy group, such as (3-glycidoxypropyl)trimethoxysilane, (3-glycidoxypropyl)triethoxysilane, [2-(3,4-epoxycyclohexyl)ethyl]trimethoxysilane, (3-glycidoxypropyl)methyldimethoxysilane, (2-glycidoxyethyl)methyldimethoxysilane, (3-glycidoxypropyl)dimethylmethoxysilane or (2-glycidoxyethyl)dimethylmethoxysilane; silanes having a (meth)acryloyloxy group, such as (3-methacryloyloxypropyl)trimethoxysilane or (3-acryloyloxypropyl)trimethoxysilane; silanes having an alkenyl group, such as vinyltrimethoxysilane, allyltrimethoxysilane or isopropenyltrimethoxysilane; silanes having a mercapto group, such as mercaptopropyltrimethoxysilane or mercaptoethyltrimethoxysilane; silanes having an aminoalkyl group, such as (3-aminopropyl)trimethoxysilane, (3-[(2-aminoethyl)amino]propyl)trimethoxysilane, (N,N-dimethylaminopropyl)trimethoxysilane or (N,N-dimethylaminoethyl)trimethoxysilane; silanes having a haloalkyl group, such as (3-chloropropyl)trimethoxysilane or trifluoropropyltrimethoxysilane; silanes having a glyceroxy group, such as (3-glyceroxypropyl)trimethoxysilane or di(3-glyceroxypropyl)dimethoxysilane; silanes having a ureido group, such as (3-ureidopropyl)trimethoxysilane, (3-ureidopropyl)methyldlmethoxysilane or (3-ureidopropyl)dimethylmethoxysilane; and silanes having a cyano group, such as cyanopropyltrimethoxysilane, cyanopropylmethyldimethoxysilane or cyanopropyldimethylmethoxysilane.

In one embodiment of the present invention, the compound of formula (IV) comprising a reactive organic group R is chosen from silanes having an epoxy group, silanes having a (meth)acryloyloxy group, silanes having an alkenyl group, silanes having a mercapto group and silanes having an aminoalkyl group.

In another embodiment of the present invention, compounds (III) and (IV) can be tetraethoxysilane and methyltrimethoxysilane, respectively.

Use may independently be made, as hydrolysis and polymerization catalysts, of basic catalysts, such as sodium hydroxide, potassium hydroxide, sodium carbonate, sodium hydrogencarbonate or amines (such as ammonia, trimethylamine, triethylamine or tetramethylammonium hydroxide), or acidic catalysts chosen from organic acids, such as citric acid, acetic acid, methanesulphonic acid, p-toluenesulphonic acid, dodecylbenzenesulphonic acid or dodecylsulphonic acid, or inorganic acids, such as hydrochloric acid, sulphuric acid or phosphoric acid. When it is present, the surfactant used can be a nonionic or anionic surfactant or a mixture of the two. Sodium dodecyl-benzenesulphonate can be used as anionic surfactant. The end of the hydrolysis is marked by the disappearance of the products (III) and (IV), which are insoluble in water, and the production of a homogeneous liquid layer.

The condensation stage (b) can use the same catalyst as the hydrolysis stage or another catalyst chosen from those mentioned above.

At the conclusion of this process, a suspension in water of fine organosilicone particles is obtained, wherein the particles can optionally be separated subsequently from the medium. The process described above can thus comprise an additional stage of filtration, for example on a membrane filter, of the product resulting from stage (b), optionally followed by a stage of centrifuging the filtrate, intended to separate the particles from the liquid medium, and then by a stage of drying the particles. Other separation methods can, of course, be employed.

In one embodiment of the present invention, the substrate made from the silicone material may be in the form of a particle with a concave surface such as a bowl.

The shape of the concave particle obtained according to the above process and its dimensions will depend in particular on the method used to bring the products into contact in stage (b).

A somewhat basic pH and introduction under cold conditions of the polymerization catalyst into the mixture resulting from stage (a) will result in portions of hollow spheres with the shape of round-bottomed "bowls", whereas a somewhat acidic pH and dropwise introduction of the mixture resulting from stage (a) into the hot polymerization catalyst will result in portions of hollow spheres having a transverse cross section with the shape of a horseshoe.

The details of the preparation of the substrate are described in JP-A-2003-128788 which is incorporated herein by reference.

Among the concave particles which can be used according to the invention, non-limiting mention may be made of: particles composed of the crosslinked organosilicone TAK-110 (crosslinked methylsilanol/silicate polymer) from Takemoto Oil & Fat, with the shape of a bowl, with a width of 2.5 μm, a height of 1.2 μm and a thickness of 150 nm (particles sold under the name NLK-506 by Takemoto Oil & Fat);

particles composed of the crosslinked organosilicone TAK-110 (crosslinked methylsilanol/silicate polymer) from Takemoto Oil & Fat, with the shape of a bowl, with a width of 2.5 μm, a height of 1.5 μm and a thickness of 350 nm;

particles composed of the crosslinked organosilicone TAK-110 (crosslinked methylsilanovsilicate polymer) from Takemoto Oil & Fat, with the shape of a bowl, with a width of 0.7 μm, a height of 0.35 μm and a thickness of 100 nm; and particles composed of the crosslinked organosilicone TAK-110 (crosslinked methylsilanol/silicate polymer) from Takemoto Oil & Fat, with the shape of a bowl, with a width of 7.5 μm, a height of 3.5 μm and a thickness of 200 nm.

The substrate may or may not be coated. It is more preferable that the substrate is coated. The material of a coating of the substrate is not limited, but an organic material such as an amino acid, an N-acylamino acid, an amido, a silicone and a modified silicone, is preferable. As the organic material, mention may be made of lauroyl lysine and acryl-modified silicone.

(Layer on Substrate)

The substrate is at least partially covered by at least one layer comprising at least one solid organic UV filter. The layer may be referred to as a coating layer. Preferably, 10% or more of the surface of the substrate is covered by the coating layer(s). More preferably, 50% or more of the surface of the substrate is covered by the coating layer(s). More preferably, 80% or more of the substrate is covered by the coating layer(s). Most preferably, the entire surface of the substrate is covered by the coating layer(s).

The thickness of the coating layer may vary depending on several factors such as the size of the substrate. Typically, the thickness of the coating layer may range from 0.001 μm to 20 μm, preferably 0.01 μm to 15 μm, more preferably from 0.03 μm to 10 μm, and more preferably from 0.1 μm to 5 μm.

If there are two or more coating layers on the substrates, the thickness and the composition of the coating layers may be the same as or different from each other.

The coating layer(s) may comprise, other than the solid organic UV filter(s), any additional material(s) such as at least one solid inorganic UV filter, at least one additional UV filter, and at least one coloring pigment. The additional material(s) may be present in an amount ranging from 1 to 50 wt % relative to the total weight of the additional material(s) and the solid organic UV filter(s).

(Solid Organic UV Filters)

As described above, the composite pigment according to the present invention has at least one coating layer which comprises at least one solid organic UV filter covering a substrate. If two or more solid organic UV filters are used, they may be the same or different, preferably the same.

The solid organic UV filter used for the present invention may be active in the UV-A and/or UV-B region, preferably in the UV-A region or in the UV-A and UV-B region. The solid organic UV filter may be hydrophilic and/or lipophilic. The solid organic UV filter is properly insoluble in solvents such as water and ethanol commonly used in cosmetics. The term "solid" means solid at 25° C. under 1 atm.

It is preferable that the solid organic UV filter is in the form of a fine particle such that the primary particle diameter thereof ranges from 1 nm to 5 μm, preferably 10 nm to 1 μm, and more preferably 10 nm to 100 nm.

If solid organic UV filter(s) in the form of fine particles is/are used, the composite pigment according to the present invention has an effect that it can provide a transparent or clear appearance, because the fine particles do not aggregate but spread on the substrate. It should be noted that free fine particles of solid organic UV filter(s) can easily aggregate.

The material of the solid organic UV filter is not limited as long as it is organic. If two or more solid organic UV filters are used, the material(s) of the solid organic UV filters may be the same or different from each other.

The solid organic UV filter may be selected from the group consisting of benzotriazole derivatives, oxanilide derivatives, triazine derivatives, triazole derivatives, vinyl-group containing amides, cinnamic acid amides, and sulfonated benzimidazoles.

One preferred class of oxanilide UV absorbers is that having the formula:

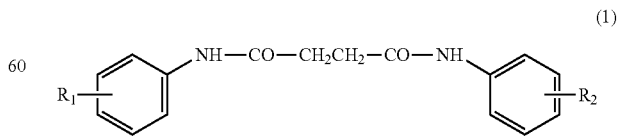

(1)

in which $R_1$ and $R_2$, independently, are $C_1$-$C_{18}$ alkyl or $C_1$-$C_{18}$ alkoxy. A preferred compound of formula (1) is N-(2-ethoxyphenyl)-N'-(2-ethylphenyl)-ethanediamide.

A preferred class of triazine compounds is that having the formula:

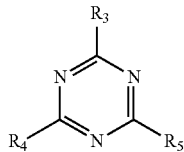

(2)

in which $R_3$, $R_4$ and $R_5$, independently, are H, OH, $C_1$-$C_{18}$ alkoxy, $NH_2$, NH—$R_6$ or $N(R_6)_2$ in which $R_6$ is $C_1$-$C_{18}$ alkyl, $OR_6$ in which $R_6$ is $C_1$-$C_{18}$ alkyl, phenyl, phenoxy or anilino, or pyrrole, in which the respective phenyl, phenoxy or anilino, or pyrrolo moieties are optionally substituted by one, two or three substitutents selected from OH, carboxy, CO—$NH_2$, $C_1$-$C_{18}$ alkyl or alkoxy, $C_1$-$C_{18}$ carboxyalkyl, $C_5$-$C_8$ cycloalkyl, a methylidenecamphor group, a group —(CH=CH)$_m$C(=O)—$OR_6$ in which m is 0 or 1 and $R_6$ has the same meaning above, or a group

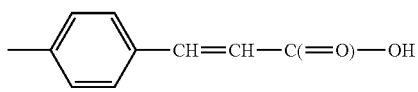

or the corresponding alkali metal, ammonium, mono-, di- or tri-$C_1$-$C_4$ alkylammonium, mono-, di- or tri-$C_2$-$C_4$ alkanolammonium salts, or the $C_1$-$C_{18}$ alkyl esters thereof.

Preferred compounds of formula (2) are those having one of the formulae:

(3)

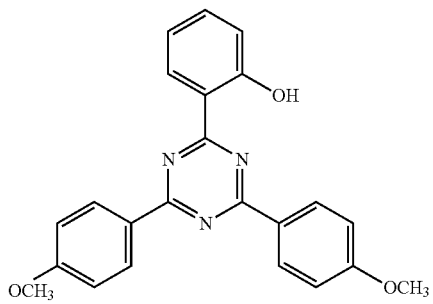

(4)

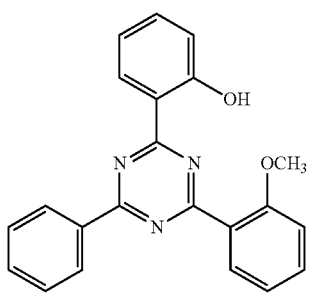

(5)

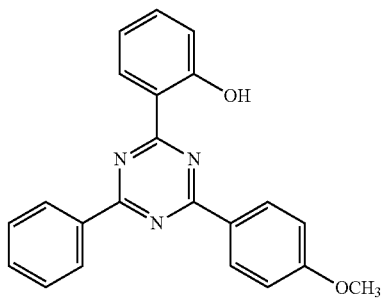

(6)

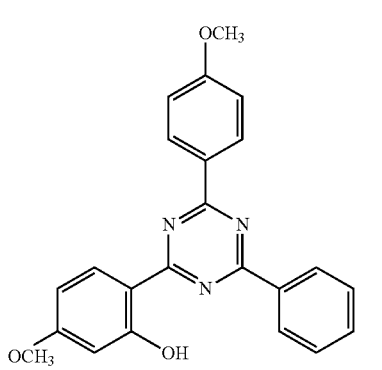

(7)

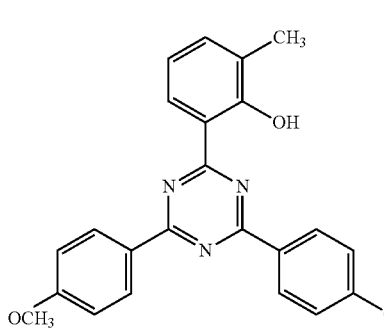

(8)

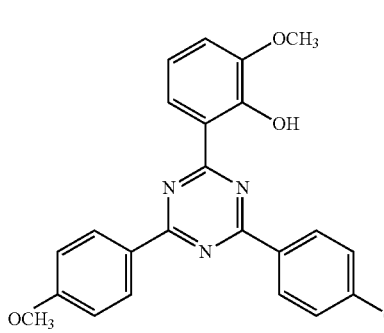

(9)

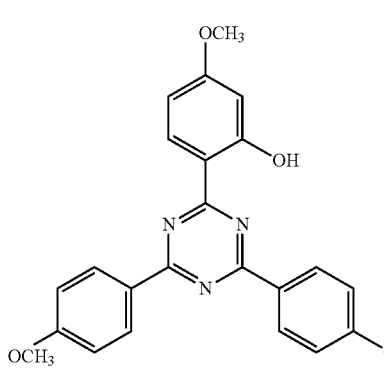

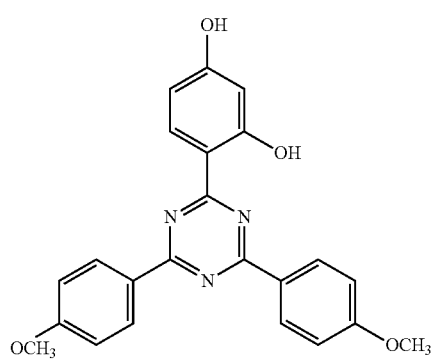
(10)
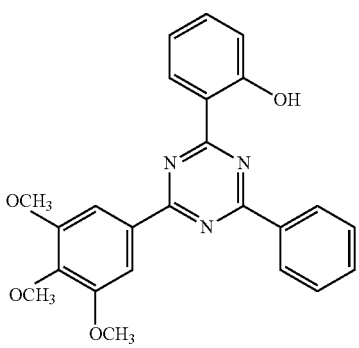
(15)
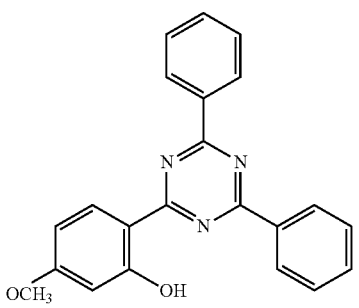
(16)
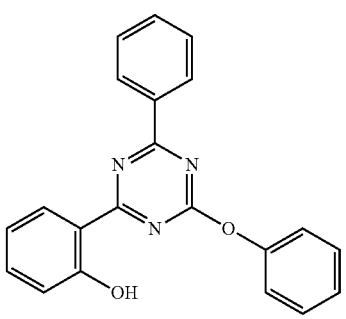
(17)
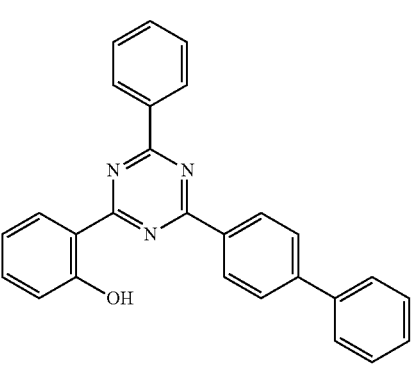
(18)

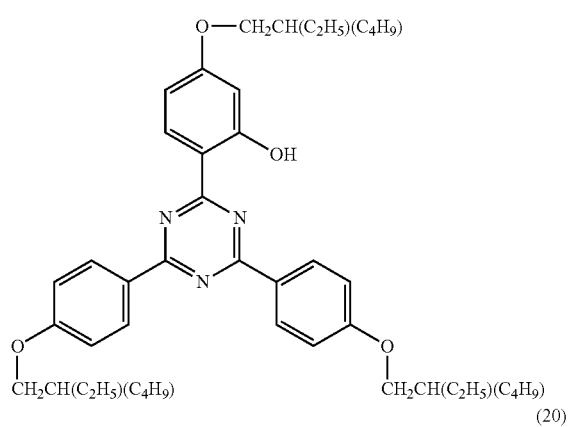
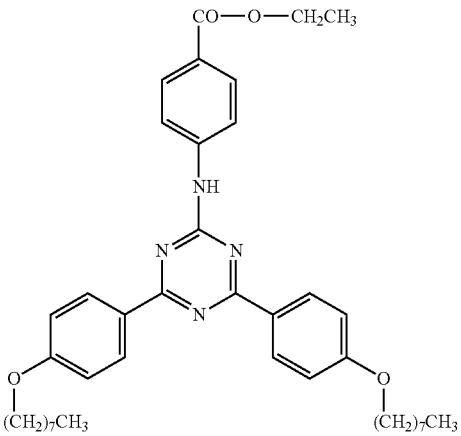
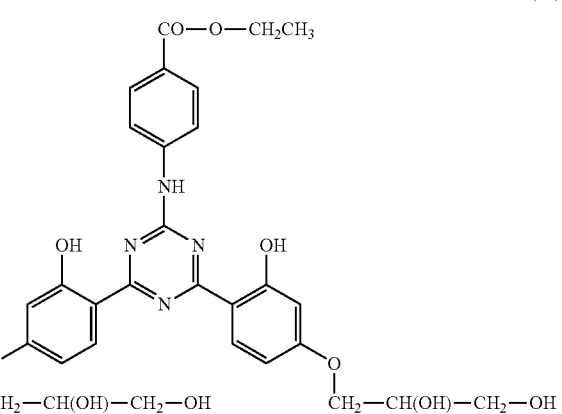
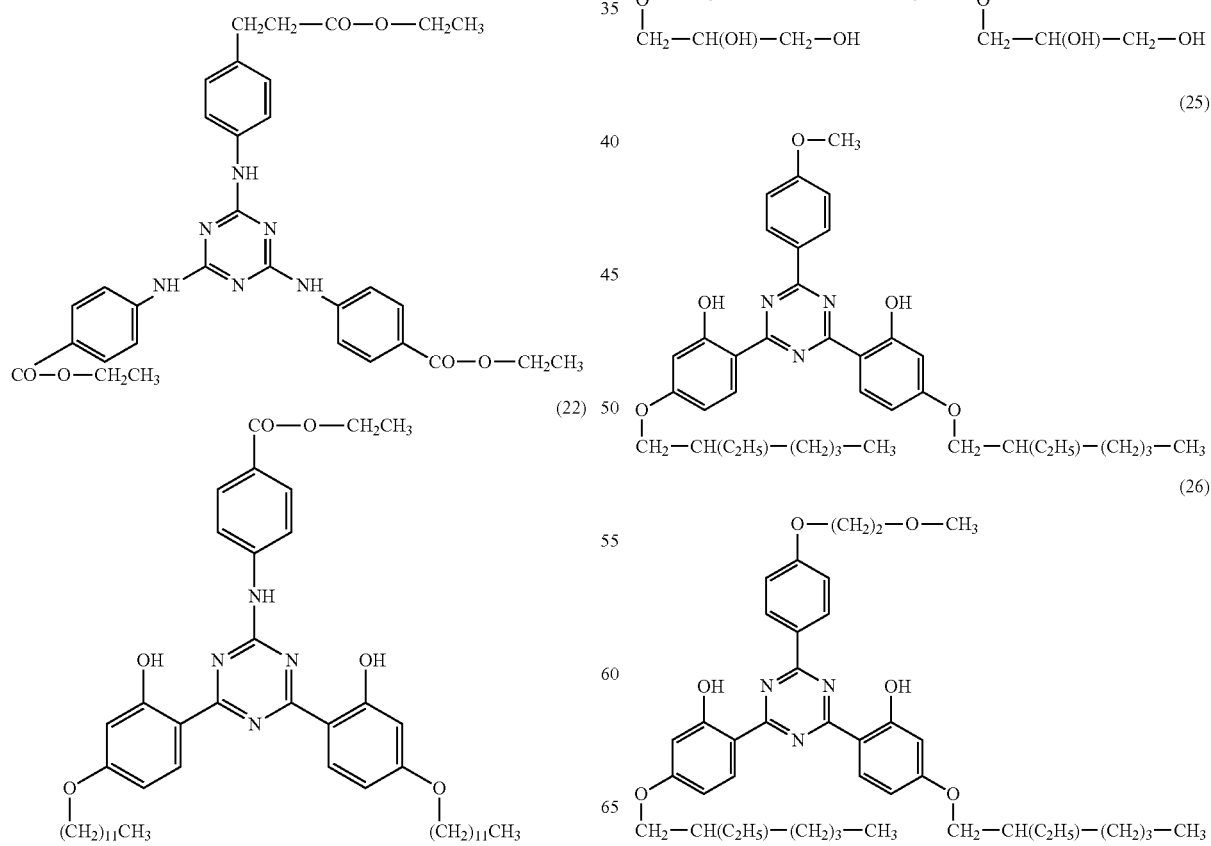

as well as 2,4,6-tris(diisobutyl-4'-aminobenzalmalonate)-s-triazine and 2,4-bis(diisobutyl-4-aminobenzalmalonate)-6-(4'-aminobenzylidenecamphor)-s-triazine. Bis-ethylhexyloxyphenol methoxyphenyl triazine, marketed under the trademark "Tinosorb S" by Ciba-Geigy is in particular preferable.

Particularly preferred compounds of formula (2) are those having the formula:

in which the individual radicals $R_7$ are the same or different and each is hydrogen; an alkali metal; an ammonium group $N(R_8)_4$ in which $R_8$ is hydrogen or an organic radical; $C_1$-$C_{20}$ alkyl; or a polyoxyethylene radical which contains from 1 to 10 ethylene oxide units and the terminal OH group of which may be etherified by a $C_1$-$C_3$ alcohol.

In relation to the compounds of formula (30), when $R_7$ is an alkali metal it is preferably potassium or, especially sodium; when $R_7$ is a group $N(R_8)_4$ in which $R_8$ has its previous meaning, it is preferably a mono-, di- or tri-$C_1$-$C_4$ alkylammonium salt, a mono-, di- or tri-$C_2$-$C_4$ alkanolammonium salt or a $C_1$-$C_{20}$ alkyl ester thereof; when $R_8$ is a $C_1$-$C_{20}$ alkyl group, it is preferably a $C_6$-$C_{12}$ alkyl group, more preferably a $C_8$-$C_9$ alkyl group, especially a 3,5,5-trimethylpentyl group or, most particularly, a 2-ethylhexyl group; and when $R_8$ is polyoxyethylene group, this preferably contains from 2-6 ethylene oxide units.

One preferred class of triazole insoluble organic UV absorbers is that having the formula:

in which $T_1$ is $C_1$-$C_{18}$ alkyl or, preferably, hydrogen; and $T_2$ is hydrogen, hydroxyl, or $C_1$-$C_{18}$ alkyl, optionally substituted by phenyl, preferably α,α-dimethylbenzyl.

A further preferred class of triazole insoluble organic UV absorbers is that having the formula:

in which $T_2$ has its previous meaning.

A still further preferred class of triazole insoluble organic UV absorbers is that having the formula:

in which $T_2$ has its previous meaning and is preferably t-butyl.

A preferred class of vinyl group-containing amide insoluble organic UV absorbers is that having the formula:

$$R_9-(Y)_m-CO-C(R_{10})=C(R_{11})-N(R_{12})(R_{13}) \qquad (34)$$

in which $R_9$ is $C_1$-$C_{18}$ alkyl, preferably $C_1$-$C_5$ alkyl, or phenyl optionally substituted by one, two or three substituents selected from OH, $C_1$-$C_{18}$ alkyl, $C_1$-$C_{18}$ alkoxy or CO—$OR_6$ in which $R_6$ has its previous meaning; $R_{10}$, $R_{11}$, $R_{12}$ and $R_{13}$ are the same or different and each is $C_1$-$C_{18}$ alkyl, preferably $C_1$-$C_5$ alkyl, or hydrogen; Y is N or O; and m has its previous meaning.

Preferred compounds of formula (34) are 4-octyl-3-penten-2-one, ethyl-3-octylamino-2-butenoate, 3-octylamino-1-phenyl-2-buten-1-one and 3-dodecylamino-1-phenyl-2-buten-1-one.

A preferred class of cinnamic acid amide insoluble organic UV absorbers is that having the formula:

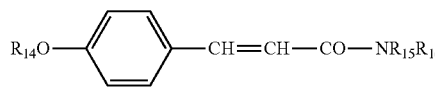

(35)

in which $R_{14}$ is hydroxy or $C_1$-$C_4$ alkoxy, preferably methoxy or ethoxy; $R_{15}$ is hydrogen or $C_1$-$C_4$ alkyl, preferably methyl or ethyl; and $R_{16}$ is —(CONH)$_m$-phenyl in which m has its previous meaning and the phenyl group is optionally substituted by one, two or three substituents selected from OH, $C_1$-$C_{18}$ alkyl, $C_1$-$C_{18}$ alkoxy or CO—$OR_6$ in which $R_6$ has its previous meaning. Preferably $R_{16}$ is phenyl, 4-methoxyphenyl or the phenylaminocarbonyl group.

A preferred class of sulfonated benzimidazole insoluble organic UV absorbers is that having the formula:

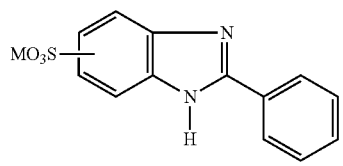

(36)

in which M is hydrogen or an alkali metal, preferably sodium, an alkaline earth metal, such as magnesium or calcium, or zinc.

In the compounds of formula (1) to (35), $C_1$-$C_{18}$ alkyl groups may be methyl, ethyl, n-propyl, isopropyl, n-butyl, isobutyl, tert-butyl, n-amyl, n-hexyl, n-heptyl, n-octyl, isooctyl, n-nonyl, n-decyl, n-undecyl, n-dodecyl, tetradecyl, hexydecyl or octadecyl; and $C_1$-$C_{18}$ alkoxy groups include methoxy, ethoxy, propoxy, butoxy, n-hexoxy, n-heptoxy, n-octoxy, isooctoxy, n-nonoxy, n-decoxy, n-undecoxy, n-dodecoxy, tetradecoxy, hexadecoxy or octadecoxy, methoxy and ethoxy being preferred.

$C_1$-$C_{18}$ carboxyalkyl includes carboxymethyl, carboxyethyl, carboxypropyl, carboxyisopropyl, carboxybutyl, carboxylsobutyl, carboxybutyl, carboxyamyl, carboxyhexyl, carboxyheptyl, carboxyoctyl, carboxylsooctyl, carboxynonyl, carboxydecyl, carboxyundecyl, carboxydodecyl, carboxytetradecyl, carboxyhexadecyl and carboxyoctadecyl, carboxymethyl being preferred.

$C_5$-$C_8$ cycloalkyl includes cyclopentyl, cyclohexyl and cyclooctyl.

The compounds of formula (1) to (35) are known. The compounds of formula (30) are described, together with their production, in U.S. Pat. No. 4,617,390.

It is preferable that the solid organic UV filter is a benzotriazole derivative, in particular, a phenylbenzotriazole derivative such as a drometrizole trisiloxane, marketed under the trademark "Silatrizole" by Rhodia Chimie or "Mexoryl XL" by L'Oreal, as represented below.

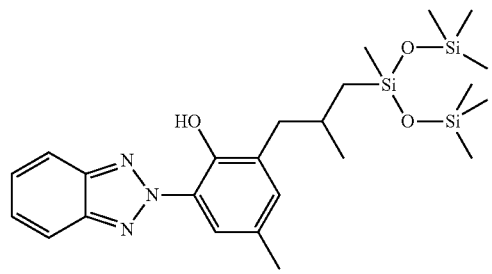 [SMILES: Cc1cc(CC(C)C[Si](C)(O[Si](C)(C)C)O[Si](C)(C)C)c(O)c(-n2nc3ccccc3n2)c1]

The solid organic UV filter(s) may be used in the composite pigment according to the present invention in proportions such that the weight ratio of the substrate to the solid organic UV filter(s) is 100:1 to 100:500, preferably 100:5 to 100:400, more preferably 100:10 to 100:200, more preferably 100:10 to 100:100, more preferably 100:10 to 100:50, and more preferably 100:10 to 100:30.

(Solid Inorganic UV Filters)

As described above, the coating layer may further comprise at least one solid inorganic UV filter. If two or more solid inorganic UV filters are used, they may be the same or different, preferably the same.

The solid inorganic UV filter used for the present invention may be active in the UV-A and/or UV-B region, preferably in the UV-B region or in the UV-A and UV-B region. It is preferable that the active UV filtering region of the solid inorganic UV filter and that of the solid organic UV filter are complementary to each other, in order to provide comprehensive UV protection. For example, it is preferable that the solid inorganic UV filter is active at least in the UV-B region and the solid organic UV filter is active at least in the UV-B region. The solid inorganic UV filter may be hydrophilic and/or lipophilic. The solid inorganic UV filter is properly insoluble in solvents such as water and ethanol commonly used in cosmetics. The term "solid" means solid at 25° C. under 1 atm.

It is preferable that the solid inorganic UV filter is in the form of a fine particle such that the primary particle diameter thereof ranges from 1 nm to 5 μm, preferably 10 nm to 1 μm, more preferably 10 nm to 100 μm, and more preferably 10 nm to 20 nm.

The inorganic UV filter may be selected from the group consisting of silicon carbide, metal oxides which may or may not be coated, and mixtures thereof.

Preferably, the inorganic UV filters are selected from pigments (mean size of the primary particles: generally from 5 nm and 100 nm, preferably from 10 nm and 50 nm) formed of metal oxides which may or may not be coated, such as, for example, pigments formed of titanium oxide (amorphous or crystalline in the rutile and/or anatase form), iron oxide, zinc oxide, zirconium oxide or cerium oxide, which are all UV photoprotective agents well known per se.

The pigments may or may not be coated. The coated pigments are pigments which have been subjected to one or more surface treatments of chemical, electronic, mechanochemical and/or mechanical nature with compounds such as described, for example, in Cosmetics & Toiletries, February 1990, Vol. 105, pp. 53-64, such as amino acids, beeswax, fatty acids, fatty alcohols, anionic surfactants, lecithins, sodium, potassium, zinc, iron or aluminum salts of fatty acids, metal alkoxides (titanium or aluminum alkoxides), polyethylene, silicones, proteins (collagen, elastin), alkanolamines, silicon oxides, metal oxides or sodium hexametaphosphate.

In a known manner, the silicones are organosilicon polymers or oligomers comprising a linear or cyclic and branched or crosslinked structure, of variable molecular weight, obtained by polymerization and/or polycondensation of suitable functional silanes and essentially composed of a repetition of main units in which the silicon atoms are connected to one another via oxygen atoms (siloxane bond), optionally substituted hydrocarbon radicals being connected directly to the said silicon atoms via a carbon atom.

The term "silicones" also encompasses the silanes necessary for their preparation, in particular alkylsilanes.

The silicones used for the coating of the pigments suitable for the present invention are preferably selected from the group consisting of alkylsilanes, polydialkylsiloxanes and polyalkylhydrosiloxanes. More preferably still, the silicones are selected from the group consisting of octyltrimethylsilane, polydimethylsiloxanes and polymethylhydrosiloxanes.

Of course, the pigments formed of metal oxides may, before their treatment with silicones, have been treated with other surfacing agents, in particular with cerium oxide, alumina, silica, aluminum compounds, silicon compounds or their mixtures.

The coated pigments are more particularly titanium oxides coated: with silica, such as the product "Sunveil" from Ikeda, with silica and with iron oxide, such as the product "Sunveil F" from Ikeda, with silica and with alumina, such as the products "Microtitanium Dioxide MT 500 SA" and "Microtitanium Dioxide MT 100 SA" from Tayca, "Tioveil" from Tioxide and "Mirasun TiW 60" from Rhodia, with alumina, such as the products "Tipaque TTO-55 (B)" and "Tipaque TTO-55 (A)" from Ishihara and "UVT 14/4" from Kemira, with alumina and with aluminum stearate, such as the product "Microtitanium Dioxide MT 100 T, MT 100 TX, MT 100 Z or MT-01" from Tayca, the products "Solaveil CT-10 W" and "Solaveil CT 100" from Uniqema and the product "Eusolex T-AVO" from Merck, with silica, with alumina and with alginic acid, such as the product "MT-100 AQ" from Tayca, with aluminum stearate, such as the product "MT-100 TV" from Tayca, primary particle diameter is 15 nm, with alumina and with aluminum laurate, such as the product "Microtitanium Dioxide MT 100 S" from Tayca, with iron oxide and with iron stearate, such as the product "Microtitanium Dioxide MT 100 F" from Tayca, with zinc oxide and with zinc stearate, such as the product "BR351" from Tayca, with silica and with alumina and treated with a silicone, such as the products "Microtitanium Dioxide MT 600 SAS", "Microtitanium Dioxide MT 500 SAS" and "Microtitanium Dioxide MT 100 SAS" from Tayca, with silica, with alumina and with aluminum stearate and treated with a silicone, such as the product "STT-30-DS" from Titan Kogyo, with silica and treated with a silicone, such as the product "UV-Titan X 195" from Kemira, with alumina and treated with a silicone, such as the products "Tipaque TTO-55 (S)" from Ishihara or "UV Titan M 262" from Kemira, with triethanolamine, such as the product "STT-65-S" from Titan Kogyo, with stearic acid, such as the product "Tipaque TTO-55 (C)" from Ishihara, or with sodium hexametaphosphate, such as the product "Microtitanium Dioxide MT 150 W" from Tayca.

Other titanium oxide pigments treated with a silicone are preferably $TiO_2$ treated with octyltrimethylsilane and for which the mean size of the individual particles is from 25 and 40 nm, such as that marketed under the trademark "T 805" by Degussa Silices, $TiO_2$ treated with a polydimethylsiloxane and for which the mean size of the individual particles is 21 nm, such as that marketed under the trademark "70250 Cardre UF TiO2SI3" by Cardre, anatase/rutile $TiO_2$ treated with a polydimethylhydrosiloxane and for which the mean size of the individual particles is 25 nm, such as that marketed under the trademark "Microtitanium Dioxide USP Grade Hydrophobic" by Color Techniques.

The uncoated titanium oxide pigments are, for example, marketed by Tayca under the trademarks "Microtitanium Dioxide MT500B" or "Microtitanium Dioxide MT600B", by Degussa under the trademark "P 25", by Wacker under the trademark "Oxyde de titane transparent PW", by Miyoshi Kasei under the trademark "UFTR", by Tomen under the trademark "ITS" and by Tioxide under the trademark "Tioveil AQ".

The uncoated zinc oxide pigments are, for example:
those marketed under the trademark "Z-cote" by Sunsmart;
those marketed under the trademark "Nanox" by Elementis; and
those marketed under the trademark "Nanogard WCD 2025" by Nanophase Technologies.

The coated zinc oxide pigments are, for example:
those marketed under the trademark "Oxide Zinc CS-5" by Toshiba (ZnO coated with polymethylhydrosiloxane);
those marketed under the trademark "Nanogard Zinc Oxide FN" by Nanophase Technologies (as a 40% dispersion in Finsolv TN, $C_{12}$-$C_{15}$ alkyl benzoate);
those marketed under the trademark "Daitopersion Zn-30" and "Daitopersion Zn-50" by Daito (dispersions in oxyethylenated polydimethylsiloxane/cyclopolymethylsiloxane comprising 30% or 50% of zinc nanooxides coated with silica and polymethylhydrosiloxane);
those marketed under the trademark "NFD Ultrafine ZnO" by Daikin (ZnO coated with phosphate of perfluoroalkyl and copolymer based on perfluoroalkylethyl as a dispersion in cyclopentasiloxane);
those marketed under the trademark "SPD-Z1" by Shin-Etsu (ZnO coated with silicone-grafted acrylic polymer dispersed in cyclodimethylsiloxane);
those marketed under the trademark "Escalol 2100" by ISP (alumina-treated ZnO dispersed in the ethylhexyl methoxycinnamate/PVP-hexadecene copolymer/methicone mixture); and
those marketed under the trademark "Fuji ZnO-SMS-10" by Fuji Pigment (ZnO coated with silica and polymethylsilsesquioxane);
those marketed under the trademark "Nanox Gel TN" by Elementis (ZnO dispersed at 55% in $C_{12}$-$C_{15}$ alkyl benzoate with hydroxystearic acid polycondensate).

The uncoated cerium oxide pigments are marketed, for example, under the trademark "Colloidal Cerium Oxide" by Rhone-Poulenc.

The uncoated iron oxide pigments are, for example, marketed by Arnaud under the trademarks "Nanogard WCD 2002 (FE 45B)", "Nanogard Iron FE 45 BL AQ", "Nanogard FE 45R AQ" or "Nanogard WCD 2006 (FE 45R)", or by Mitsubishi under the trademark "TY-220".

The coated iron oxide pigments are, for example, marketed by Arnaud under the trademarks "Nanogard WCD 2008 (FE 45B FN)", "Nanogard WCD 2009 (FE 45B 556)", "Nanogard FE 45 BL 345" or "Nanogard FE 45 BL" or by BASF under the trademark "Oxyde de fer transparent".

Mention may also be made of mixtures of metal oxides, in particular of titanium dioxide and of cerium dioxide, including the mixture of equal weights of titanium dioxide coated with silica and of cerium dioxide coated with silica marketed by Ikeda under the trademark "Sunveil A", and also the mixture of titanium dioxide and of zinc dioxide coated with alumina, with silica and with silicone, such as the product "M 261" marketed by Kemira, or coated with alumina, with silica and with glycerol, such as the product "M 211" marketed by Kemira.

The coated pigments are preferable because the coating may function as a binder for fixing the pigments on a substrate. In particular, titanium oxide coated with aluminum stearate such as the product "MT-100 TV" from Tayca is preferable.

If solid inorganic UV filter(s) in the form of fine particles is/are used, the composite pigment according to the present invention has an effect that it can provide not a white appearance but a transparent or clear appearance, because the fine particles do not aggregate but spread on the substrate. It should be noted that free fine particles of solid inorganic UV filter(s) easily aggregate to give white appearance to the skin.

Further, if solid inorganic UV filter(s) in the form of fine particles is/are used, the composite pigment according to the present invention has an additional effect that the particles of the solid inorganic UV filter(s) can be well dispersed in the coating layer due to the presence of the solid organic UV filter(s), and therefore, the solid inorganic UV filter(s) can be present in the coating layer in the form of primary particles. On the other hand, in the above case, the particles of the solid organic UV filter(s) can also be well dispersed in the coating layer due to the presence of the solid inorganic UV filter(s), and therefore, the solid organic UV filter(s) can be present in the coating layer in the form of primary particles. Accordingly, the UV filtering effects by the solid inorganic UV filter(s) preferably in the UVB region as well as the solid organic UV filter(s) can be enhanced.

The solid inorganic UV filter(s) may be used in the composite pigment according to the present invention in proportions such that the weight ratio of the substrate to the solid inorganic UV filter(s) is 100:1 to 100:500, preferably 100:5 to 100:400, more preferably 100:10 to 100:200, more preferably 100:10 to 100:100, more preferably 100:10 to 100:50, and more preferably 100:10 to 100:30.

(Additional UV Filters)

As described above, the coating layer may further comprise at least one additional UV filter. If two or more additional UV filters are used, they may be the same or different, preferably the same.

The additional UV filter used for the present invention may be active in the UV-A and/or UV-B region. The additional UV filter may be hydrophilic and/or lipophilic. The additional UV filter is preferably made from an organic substance which is in the form of a liquid. The term "liquid" means liquid at 25° C. under 1 atm.

The additional UV filter may be selected from the group consisting of anthranilic derivatives; dibenzoylmethane derivatives; liquid cinnamic derivatives; salicylic derivatives; camphor derivatives; benzophenone derivatives; β,β-diphenylacrylate derivatives; liquid triazine derivatives; liquid benzotriazole derivatives; benzalmalonate derivatives; benzimidazole derivatives; imidazoline derivatives; bis-benzoazolyl derivatives; p-aminobenzoic acid (PABA) and derivatives thereof; methylenebis(hydroxyphenylbenzotriazole) derivatives; benzoxazole derivatives; screening polymers and screening silicones; dimers derived from α-alkylstyrene; 4,4-diarylbutadienes; octocrylene and derivatives thereof, guaiazulene and derivatives thereof, rutin and derivatives thereof, flavonoids, biflavonoids, oryzanol and derivatives thereof, quinic acid and derivatives thereof, phenols, retinol, cysteine, aromatic amino acid, peptides having an aromatic amino acid residue, and mixtures thereof.

Mention may be made, as examples of additional UV filters, of those denoted below under their INCI names, and mixtures thereof.

Anthranilic derivatives: Menthyl anthranilate, marketed under the trademark "Neo Heliopan MA" by Haarmann and Reimer.

Dibenzoylmethane derivatives: Butyl methoxydibenzoylmethane, marketed in particular under the trademark "Parsol 1789" by Hoffmann-La Roche; and Isopropyl dibenzoylmethane.

Liquid cinnamic derivatives: Ethylhexyl methoxycinnamate, marketed in particular under the trademark "Parsol MCX" by Hoffmann-La Roche; Isopropyl methoxycinnamate; Isopropoxy methoxycinnamate; Isoamyl methoxycinnamate, marketed under the trademark "Neo Heliopan E 1000" by Haarmann and Reimer; Cinoxate (2-ethoxyethyl-4-methoxy cinnamate); DEA Methoxycinnamate; Diisopropyl methylcinnamate; and Glyceryl ethylhexanoate dimethoxycinnamate.

Salicylic derivatives: Homosalate (homomentyl salicylate), marketed under the trademark "Eusolex HMS" by Rona/EM Industries; Ethylhexyl salicylate, marketed under the trademark "Neo Heliopan OS" by Haarmann and Reimer; Glycol salicylate; Butyloctyl salicylate; Phenyl salicylate; Dipropyleneglycol salicylate, marketed under the trademark "Dipsal" by Scher; and TEA Salicylate, marketed under the trademark "Neo Heliopan TS" by Haarmann and Reimer.

Camphor derivatives, in particular, benzylidenecamphor derivatives: 3-Benzylidene camphor, manufactured under the trademark "Mexoryl SD" by Chimex; 4-Methylbenzylidene camphor, marketed under the trademark "Eusolex 6300" by Merck; Benzylidene camphor sulfonic acid, manufactured under the trademark "Mexoryl SL" by Chimex; Camphor benzalkonium methosulfate, manufactured under the trademark "Mexoryl SO" by Chimex; Terephthalylidene dicamphor sulfonic acid, manufactured under the trademark "Mexoryl SX" by Chimex; and Polyacrylamidomethyl benzylidene camphor, manufactured under the trademark "Mexoryl SW" by Chimex.

Benzophenone derivatives: Benzophenone-1 (2,4-dihydroxybenzophenone), marketed under the trademark "Uvinul 400" by BASF; Benzophenone-2 (Tetrahydroxybenzophenone), marketed under the trademark "Uvinul D50" by BASF; Benzophenone-3 (2-hydroxy-4-methoxybenzophenone) or Oxybenzone, marketed under the trademark "Uvinul M40" by BASF; Benzophenone-4 (Hydroxymethoxy benzophenene sulfonic acid), marketed under the trademark "Uvinul MS40" by BASF; Benzophenone-5 (Sodium hydroxymethoxy benzophenone Sulfonate); Benzophenone-6 (Dihydroxy dimethoxy benzophenone); marketed under the trademark "Helisorb 11" by Norquay; Benzophenone-8, marketed under the trademark "Spectra-Sorb UV-24" by American Cyanamid; Benzophenone-9 (Disodium dihydroxy dimethoxy benzophenonedisulfonate), marketed under the trademark "Uvinul DS-49" by BASF; Benzophenone-12, and n-Hexyl 2-(4-diethylamino-2-hydroxybenzoyl)benzoate.

β,β-Diphenylacrylate derivatives: Octocrylene, marketed in particular under the trademark "Uvinul N539" by BASF; and Etocrylene, marketed in particular under the trademark "Uvinul N35" by BASF.

Liquid triazine derivatives: Diethylhexyl butamido triazone, marketed under the trademark "Uvasorb HEB" by Sigma 3V; 2,4,6-Tris(dineopentyl 4'-aminobenzalmalonate)-s-triazine; and the symmetrical triazine screening agents described in U.S. Pat. No. 6,225,467, WO 2004/085412 (see compounds 6 and 9) or the document "Symmetrical Triazine Derivatives", IP.COM Journal, IP.COM INC, WEST HENRIETTA, NY, US (20 Sep. 2004), in particular the 2,4,6-tris (biphenyl)-1,3,5-triazines (especially 2,4,6-tris(biphenyl-4-yl)-1,3,5-triazine) and 2,4,6-tris(terphenyl)-1,3,5-triazine, which is taken up again in WO 06/035000, WO 06/034982, WO 06/034991, WO 06/035007, WO 2006/034992 and WO 2006/034985.

Liquid benzotriazole derivatives, in particular, phenylbenzotriazole derivatives: 2-(2H-benzotriazole-2-yl)-6-dodecyl-4-methylpheno, branched and linear; and those described in U.S. Pat. No. 5,240,975.

Benzalmalonate derivatives: Dineopentyl 4'-methoxybenzalmalonate, and Polyorganosiloxane comprising benzalmalonate functional groups, such as Polysilicone-15, marketed under the trademark "Parsol SLX" by Hoffmann-LaRoche.

Benzimidazole derivatives, in particular, phenylbenzimidazole derivatives: Phenylbenzimidazole sulfonic Acid, marketed in particular under the trademark "Eusolex 232" by Merck, and Disodium Phenyl Dibenzimidazole tetrasulfonate, marketed under the trademark "Neo Heliopan AP" by Haarmann and Reimer.

Imidazoline derivatives: Ethylhexyl dimethoxybenzylidene Dioxoimidazoline propionate.

bis-Benzoazolyl derivatives: The derivatives as described in EP-669,323 and U.S. Pat. No. 2,463,264.

para-Aminobenzoic acid and derivatives thereof: PABA (p-Aminobenzoic acid), Ethyl PABA, Ethyl dihydroxypropyl PABA, Penthyl dimethyl PABA, Ethylhexyl dimethyl PABA, marketed in particular under the trademark "Escalol 507" by ISP, Glyceryl PABA, and PEG-25 PABA, marketed under the trademark "Uvinul P25" by BASF.

Methylenebis(hydroxyphenylbenzotriazole) derivatives: Methylene bis-benzotriazolyl tetramethylbutylphenol, marketed in the solid form under the trademark "Mixxim BB/100" by Fairmount Chemical or in the micronized form in aqueous dispersion under the trademark "Tinosorb M" by Ciba Specialty Chemicals, and the derivatives as described in U.S. Pat. Nos. 5,237,071, 5,166,355, GB-2,303,549, DE-197, 26,184 and EP-893,119.

Benzoxazole derivatives: 2,4-bis[5-1(dimethylpropyl) benzoxazol-2-yl-(4-phenyl)imino]-6-(2-ethylhexyl)imino-1, 3,5-triazine, marketed under the trademark of Uvasorb K2A by Sigma 3V.

Screening polymers and screening silicones: The silicones described in WO 93/04665.

Dimers derived from α-alkylstyrene: The dimers described in DE-19855649.

4,4-Diarylbutadiene Derivatives: 1,1-Dicarboxy(2,2'-dimethylpropyl)-4,4-diphenylbutadiene.

Octocrylene and derivatives thereof: Octocrylene.

Quaiazulene and derivatives thereof: Guaiazulene, and Sodium Guaiazulene Sulfonate.

Rutin and derivatives thereof: Rutin, and Glucosylrutin.

Flavonoids: Robustin (isoflavonoid), Genistein (flavonoid), Tectochrysin (flavonoid), and Hispidone (flavonoid).

Biflavonoids: Lanceolatin A, Lanceolatin B, and Hypnumbiflavonoid A.

Oryzanol and derivatives thereof: Γ-oryzanol.

Quinic acid and derivatives thereof: Quinic acid.

Phenols: Phenol.

Retinols: Retinol.

Cysteines: L-Cysteine.

Peptides having an aromatic amino acid residue: Peptides having tryptophan, tyrosine or phenylalanine.

The preferred organic UV screening agents are selected from: Ethylhexyl methoxycinnamate, Homosalate, Ethylhexyl salicylate, Octocrylene, Phenylbenzimidazole sulfonic acid, Benzophenone-3, Benzophenone-4, Benzophenone-5, n-Hexyl 2-(4-diethylamino-2-hydroxybenzoyl)benzoate, 4-Methylbenzylidene camphor, terephthalylidene Dicamphor sulfonic acid, Disodium phenyl dibenzimidazole tetrasulfonate, Ethylhexyl triazone, bis-Ethylhexyloxyphenol methoxyphenyl triazine, Diethylhexyl butamido triazone, 2,4,6-Tris(dineopentyl 4'-aminobenzalmalonate)-s-triazine, 2,4,6-Tris(diisobutyl 4'-aminobenzalmalonate)-s-triazine, 2,4,6-Tris(biphenyl-4-yl)-1,3,5-triazine, 2,4,6-Tris(terphenyl)-1,3,5-triazine, Methylene bis-benzotriazolyl tetramethylbutylphenol, Polysilicone-15, Dineopentyl 4'-methoxybenzalmalonate, 1,1-Dicarboxy(2,2'-dimethylpropyl)-4,4-diphenylbutadiene, 2,4-bis[5-1(dimethylpropyl)benzoxazol-2-yl-(4-phenyl)imino]-6-(2-ethylhexyl)imino-1,3,5-triazine, and their mixtures.

More preferable organic UV filter is ethylhexyl methoxycinnamate.

The additional UV filter(s) may be used in the composite pigment according to the present invention in proportions such that the weight ratio of the substrate to the additional UV filter(s) is 100:1 to 100:500, preferably 100:5 to 100:400, more preferably 100:10 to 100:200, more preferably 100:10 to 100:100, more preferably 100:10 to 100:50, and more preferably 100:10 to 100:30.

(Coloring Pigments)

As described above, the coating layer may further comprise at least one coloring pigment.

The term "coloring pigment(s)" should be understood as meaning white or colored, inorganic or organic particle(s) of any shape which is/are insoluble and is/are intended to color a composition comprising them.

If coloring pigment(s) is/are used, the composite pigment according to the present invention has an effect in that it can provide a clearer appearance with high chroma, because the coloring pigments do not aggregate but spread on the substrate. It should be noted that free coloring pigments easily aggregate to give a dark appearance with low chroma to the skin.

The pigments can be white or colored, inorganic and/or organic.

Among the inorganic pigments that may be used, non-limiting mention may be made of titanium dioxide, optionally surface treated, zirconium or cerium oxide, as well as zinc, (black, yellow or red) iron or chromium oxide, manganese violet, ultramarine blue, chromium hydrate and ferric blue, or metal powders, such as aluminum powder or copper powder. The pigments can also be chosen from nanopigments formed of metal oxides, such as titanium dioxide, zinc oxide, iron oxide, zirconium oxide, and cerium oxide, and mixtures thereof. The term "nanopigments" is understood to mean pigments having a mean particle size ranging from 1 nm to 500 nm, such as particle sizes ranging from 10 nm to 100 nm.

Among organic pigments that may be used, non-limiting mention may be made of carbon black, pigments of D&C type and lakes, such as lakes-based on cochineal carmine and on barium, strontium, calcium or aluminum. For example, Red 202 (Calcium bis[2-(3-carboxy-2-hydroxynephthylazo)-5-methylbenzenesulfonate) may be used as the pigment of D&C type.

Preferably, the coloring pigment is chosen from titanium dioxide, zirconium oxide, cerium oxide, zinc oxide, iron oxide, chromium oxide, manganese violet, ultramarine blue, chromium hydrate, ferric blue, aluminum powder, copper powder, carbon black, pigments of D&C type, lakes, pearlescent pigments, and mixtures thereof.

The term "pearlescent pigments" should be understood as meaning iridescent particles of any shape, such as particles produced by certain shellfish in their shells or else synthesized.

The pearlescent agents can be chosen from white pearlescent agents, such as mica covered with titanium dioxide or with bismuth oxychloride; colored pearlescent agents, such as titanium oxide-coated mica covered with iron oxide, titanium oxide-coated mica covered with ferric blue or chromium oxide, or titanium oxide-coated mica covered with an organic pigment of the above-mentioned type; and pearlescent agents based on bismuth oxychloride.

The coloring pigment(s) may be used in the composite pigment according to the present invention in proportions such that the weight ratio of the substrate to the coloring pigment(s) is 100:1 to 100:500, preferably 100:5 to 100:400, more preferably 100:10 to 100:200, more preferably 100:10 to 100:100, more preferably 100:10 to 100:50, and more preferably 100:10 to 100:30.

(Method for Preparing Composite Pigment)

The composite pigment according to the present invention can be prepared by subjecting a substrate, at least one solid organic UV filter, and optionally at least one solid inorganic UV filter, at least one additional UV filter and/or at least one coloring pigment, to a mechanochemical fusion process.

The mechanochemical fusion process means a process in which mechanical power such as impact force, friction force or shear force is applied to a plurality of subjects to cause fusion between the subjects.

The mechanochemical fusion process may be performed by, for example, an apparatus comprising a rotating chamber and a fixed inner piece with a scraper, such as a mechanofusion system marketed by Hosokawa Micron Corporation in Japan.

It is preferable to use a hybridizer process as the mechanochemical fusion process.

The hybridizer process was developed in the 1980s. The hybridizer process is a class of mechanochemical fusion processes in which strong mechanical power is applied to a plurality of particles to cause mechanochemical reaction to form a composite particle.

According to the hybridizer process, the mechanical power is imparted by a high speed rotor which can have a diameter from 10 cm to 1 m, and can rotate at a speed of 1,000 rpm to 100,000 rpm. Therefore, the hybridizer process can be defined as a mechanochemical fusion process using such a high speed rotor. The hybridizer process is performed in air or under dry conditions. Thus, due to the high speed rotation of the rotor, high speed air flow may be generated near the rotor. However, some liquid materials may be subjected to the hybridizer process together with solid materials. The term "hybridizer process" has been used as a technical term.

The hybridizer process can be performed by using a hybridization system marketed by, for example, Nara Machinery in Japan, in which at least two types of particles, typically core particles and fine particles, are fed into a hybridizer equipped with a high speed rotor having a plurality of blades in a chamber under dry conditions, and the particles are dispersed in the chamber and mechanical and thermal energy (e.g., compression, friction and shear stress) are imparted to the particles for a relatively short period of time such as 1 to 10 minutes, preferably 1 to 5 minutes. As a result, one type of particles (e.g., fine particles) is embedded or fixed on the other type of particle (e.g., core particle) to form a composite particle. It is preferable that the particles have been subjected to electrostatic treatment(s) such as shaking to form an "ordered mixture" in which one type of particles are spread to cover the other type of particle. The hybridizer process can also be performed by using a theta composer marketed by Tokuju Corporation in Japan.

According to the present invention, a substrate and solid organic UV filter(s) as well as optionally additional material(s) such as solid inorganic UV filter(s), additional UV filter(s) and coloring pigment(s) if necessary, can be fed into such a hybridizer to form a composite pigment. The hybridizer process can be performed by using a rotor rotating at about 8,000 rpm (100 m/sec) for about 5 minutes.

If solid organic UV filter(s) and any of solid inorganic UV filter(s), additional UV filter(s) and coloring pigment(s) are used for the composite pigment according to the present invention, they can be used in proportions such that the weight ratio of the substrate to the solid organic UV filter(s) and any of solid inorganic UV filter(s), additional UV filter(s) and coloring pigment(s) is 100:1 to 100:500, preferably 100:5 to 100:400, more preferably 100:10 to 100:200, more preferably 100:10 to 100:100, more preferably 100:10 to 100:50, and more preferably 100:10 to 100:30.

The hybridizer process enables to provide a composite pigment in which a substrate is at least in part covered by at least one layer comprising at least one solid organic UV filter, and optionally solid inorganic UV filter(s), additional UV filter(s) and coloring pigment(s).

Furthermore, the hybridizer process can provide ordered array (e.g., uniform coverage) of solid organic UV filter(s) and optionally solid inorganic UV filter(s), additional UV filter(s) and coloring pigment(s) on a substrate and provides strong bonds at the surface of the substrate and a layer comprising the solid organic UV filter(s) and optionally solid inorganic UV filter(s), additional UV filter(s) and coloring pigment(s).

It should be noted that the hybridizer process is quite different from other processes using, for example, a beads mill and a jet mill. In fact, a beads mill causes pulverization or aggregation of core particles, and a jet mill causes pulverization of core particles and uniform coating of a core particle by fine particles.

If necessary, an additional process for further coating the composite pigment by additional UV filter(s) and/or coloring material(s) may be performed. As a result of this additional process, the composite pigment according to the present invention may be coated with a further layer comprising UV filter(s) and/or coloring material(s), preferably consisting of UV filter(s) and/or coloring material(s).

(Cosmetic Composition)

The composite pigment, as described above, can be present in the composition according to the present invention in an amount ranging from 0.01% to 99% by weight, preferably 0.1% to 50% by weight, and more preferably 1% to 30% by weight, relative to the total weight of the composition.

Preferably, the composite pigment according to the present invention can be used in cosmetic compositions to be applied to keratin substances such as skin, hair, and nails, providing UV shielding effects, and optionally coloring effects, because the composite pigment can exhibit good UV filtering effects possibly with a transparent or clear appearance and optionally good coloring effects such as a more transparent or clear coloring, without the risk of affecting the keratin substances.

The cosmetic composition according to the present invention may further comprise a filler and an oil.

As used herein, the term "filler" should be understood as meaning colorless natural or synthetic particles of any shape which are insoluble in the medium of the composition, whatever the temperature at which the composition is manufactured. Thus, the filler is different from the coloring pigment as described above.

The fillers may be inorganic or organic and of any shape (for instance, platelet, spherical, and oblong shapes) and with any crystallographic form (for example, sheet, cubic, hexagonal, orthorhombic, and the like). Examples of suitable additional fillers include, but are not limited to, talc; mica; silica; kaolin; powders of polyamide such as Nylon®; poly-β-3-alanine powders; polyethylene powders; polyurethane powders, such as the powder formed of hexamethylene diisocyanate and trimethylol hexyllactone copolymer sold under the name Plastic Powder D-400 by Toshiki; the powders formed of tetrafluoroethylene polymers (Teflon®); lauroyllysine; starch; boron nitride; polymeric hollow microspheres, such as microspheres of poly(vinylidene chloride)/acrylonitrile, for example Expancel® (Nobel Industrie), and microspheres of acrylic acid copolymers; silicone resin powders, for example, silsesquioxane powders (for instance, silicone resin powders disclosed in European Patent No. 0 293 795 and Tospearls® from Toshiba); poly(methyl methacrylate) particles; precipitated calcium carbonate; magnesium carbonate; basic magnesium carbonate; hydroxyapatite; hollow silica microspheres; glass microcapsules; ceramic microcapsules; metal soaps derived from organic carboxylic acids comprising from 8 to 22 carbon atoms, for example, from 12 to 18 carbon atoms, such as zinc stearate, magnesium stearate, lithium stearate, zinc laurate, and magnesium myristate; barium sulphate; and mixtures thereof.

The filler may be present in the composition in an amount ranging from 0.1% to 80% by weight, with respect to the total weight of the composition, for example, from 1% to 25% by weight, or from 3% to 15% by weight.

The term "oil" is understood to mean a fatty substance which is liquid at ambient temperature (25° C.)

Use may be made, as oils which can be used in the composition of the invention, for example, of hydrocarbon oils of animal origin, such as perhydrosqualene (or squalane); hydrocarbon oils of vegetable origin, such as triglycerides of caprylic/capric acids, for example those marketed by Stearineries Dubois or those marketed under the trademarks Miglyol 810, 812 and 818 by Dynamit Nobel, or oils of vegetable origin, for example sunflower, maize, soybean, cucumber, grape seed, sesame, hazelnut, apricot, macadamia, arara, coriander, castor, avocado or jojoba oil or shea butter oil; synthetic oils; silicone oils, such as volatile or non-volatile polymethylsiloxanes (PDMSs) comprising a linear or cyclic silicone chain which are liquid or paste at ambient temperature; fluorinated oils, such as those which are partially hydrocarbon and/or silicone, for example those described in JP-A-2-295912; ethers, such as dicaprylyl ether (CTFA name); and esters, such as benzoate $C_{12}$-$C_{15}$ fatty alcohols (Finsolv TN from Finetex); arylalkyl benzoate derivatives, such as 2-phenylethyl benzoate (X-Tend 226 from ISP); amidated oils, such as isopropyl N-lauroylsarcosinate (Eldew SL-205 from Ajinomoto), and their mixtures.

The oily phase can also comprise one or more fatty substances selected, for example, from fatty alcohols (cetyl alcohol, stearyl alcohol, cetearyl alcohol), fatty acids (stearic acid) or waxes (paraffin wax, polyethylene waxes, carnauba wax, beeswax). The oily phase can comprise lipophilic gelling agents, surfactants or also organic or inorganic particles.

The oily phase can preferably represent from 1 to 70% of oil by weight, with respect to the total weight of the composition.

The composition according to the present invention may further comprise at least one additional conventional cosmetic ingredient which may be chosen, for example, from hydrophilic or lipophilic gelling and/or thickening agents, surfactants, antioxidants, fragrances, preservatives, neutralizing agents, sunscreens, vitamins, moisturizing agents, self-tanning compounds, antiwrinkle active agents, emollients, hydrophilic or lipophilic active agents, agents for combating pollution and/or free radicals, sequestering agents, film-forming agents, dermo-decontracting active agents, soothing agents, agents which stimulate the synthesis of dermal or epidermal macromolecules and/or which prevent their decomposition, antiglycation agents, agents which combat irritation, desquamating agents, depigmenting agents, antipigmenting agents, propigmenting agents, NO-synthase inhibitors, agents which stimulate the proliferation of fibroblasts and/or keratinocytes and/or the differentiation of keratinocytes, agents which act on microcirculation, agents which act on energy metabolism of the cells, healing agents, and mixtures thereof.

The composition according to the present invention may be in various forms, for example, suspensions, dispersions, solutions, gels, emulsions, such as oil-in-water (O/W), water-in-oil (W/O), and multiple (e.g., W/O/W, polyol/O/W, and O/W/O) emulsions, creams, foams, sticks, dispersions of vesicles, for instance, of ionic and/or nonionic lipids, two-phase and multi-phase lotions, sprays, powders, and pastes. The composition may be anhydrous; for example, it can be an anhydrous paste or stick. The composition may also be a leave-in composition.

According to one embodiment, the composition according to the present invention may be in the form of an anhydrous composition such as a liquid or solid oily composition or a powdery composition.

According to another embodiment, the composition according to the present invention may be in the form of, for example, a compact powder, a lotion, a serum, a milk, a cream, a base foundation, an undercoat, a make-up base coat, a foundation, a face powder, cheek rouge, a lipstick, a lip cream, an eye shadow, an eyeliner, a loose powder, a concealer, a nail coat, mascara, a sunscreen and the like.

It is to be understood that a person skilled in the art can choose the appropriate presentation form, as well as its method of preparation, on the basis of his/her general knowledge, taking into account the nature of the constituents used, for example, their solubility in the vehicle, and the application envisaged for the composition.

EXAMPLES

The present invention will be described in more detail by way of examples, which however should not be construed as limiting the scope of the present invention.

Examples 1 to 5 and Comparative Examples 1 and 2

The components shown in Tables 1 and 2 were subjected to a hybridizer process using a Hybridizer equipped with a high speed rotor having a plurality of blades in a chamber in dry conditions, marketed by Nara Machinery Co., Ltd. in Japan to obtain a composite pigment.

In detail, for each of Examples 1 to 5 and Comparative Examples 1 and 2, the components shown in Tables 1 and 2 were mixed at the mixing ratio (the numerals in Tables 1 and 2 are based on parts by weight) shown in Tables 1 and 2 in a plastic bag by hand shaking for a short period of time. The mixture was put in the Hybridizer, and the rotor was revolved at 8,000 rpm (100 m/s linear velocity) for 5 minutes.

TABLE 1

|  | Core | | | | UV Filter | | |
| --- | --- | --- | --- | --- | --- | --- | --- |
|  | NLK | Mica* | PMMA | POL | $TiO_2$ | OMC | Mexoryl |
| Ex. 1 | 100 | — | — | — | 40 | — | 10 |
| Ex. 2 | 100 | — | — | — | 40 | 10 | 10 |
| Ex. 3 | — | 100 | — | — | 20 | 20 | 20 |
| Ex. 4 | — | — | 100 | — | 20 | 20 | 20 |
| Ex. 5 | — | — | — | 100 | — | — | 20 |

TABLE 2

|  | Core | | UV Filter |
| --- | --- | --- | --- |
|  | NLK | Mica* | $TiO_2$ |
| Comp. Ex. 1 | 100 | — | 40 |
| Comp. Ex. 2 | — | 100 | 40 |

NLK: A bowl-like particle of methylsilanol/silicate crosspolymer, NLK 506 marketed by Takemoto Oil & Fat Co., Ltd. in Japan
Mica*: Synthetic mica in the form of a plate
PMMA: A spherical particle of polymethylmethacrylate
POL: A particle of a composite of porous $CaCO_3$ and hydroxyapatite, Poronex C marketed by Maruo Calcium Co., Ltd. in Japan
$TiO_2$: MT-100 TV marketed by Tayca Corporation in Japan
OMC: Ethylhexyl methoxycinnamate
Mexoryl: Drometrizole trisiloxane

[Particle Size Change Determination]

The change in the particle size before and after the hybridizer process was measured by a MASTERSIZER 2000 (Malvern Industries Ltd., UK) for Examples 1 to 5 and Comparative Examples 1 and 2. The particle size before the hybridizer process corresponds to the particle size of a "mixture" in which UV filter(s) is/are spread to cover the core particle after the above hand shaking. The results are shown in Table 3. In Table 3, [Mixture] means a mixture of the components shown in Tables 1 and 2 which has not yet been subjected to the hybridizer process.

TABLE 3

|  | Before (μm) [Mixture] | After (μm) [Composite Pigment] | After/Before Ratio (%) |
| --- | --- | --- | --- |
| Ex. 1 | 4.8 | 2.7 | 57 |
| Ex. 2 | 3.4 | 3.1 | 92 |
| Ex. 3 | 17.8 | 11.6 | 65 |
| Ex. 4 | 9.6 | 6.4 | 67 |
| Ex. 5 | 5.3 | 3.9 | 74 |
| Comp. Ex. 1 | 4.6 | 2.4 | 52 |
| Comp. Ex. 2 | 5.7 | 4.3 | 76 |

It is clear from Table 3 that the particle size of each of the core particles used in Examples 1 to 5 and Comparative Examples 1 and 2 is reduced by 48 to 8%, due to the mechanical stress in the mechanochemical fusion process such as a hybridizer process.

TWC Foundation

A Two Way Cake (TWC) foundation including the above "mixture" before the above hybridization process or a composite pigment obtained by the above hybridization process was prepared for each of Examples 1 to 5 and Comparative Examples 1 and 2 by mixing the components shown in Table 4.

TABLE 4

|  | Wt % |
| --- | --- |
| Synthetic mica | 36.0 |
| Titanium oxide | 2.7 |
| Yellow iron oxide | 1.4 |
| Black iron oxide | 0.1 |
| Red iron oxide | 0.3 |
| Spherical silica | 4.5 |
| Talc | 37.8 |
| Mixture or Composite Pigment | 10.0 |
| Oil | 7.2 |
| Total | 100 |

In Table 4, "Mixture" means a mixture of the components shown in Tables 1 and 2 which has not yet been subjected to the hybridizer process, and "Composite Pigment" means a composite pigment obtained by the hybridizer process for the components shown in Tables 1 and 2.

[UVA and UVB Absorbance Determination]

Absorbance of UV waves of the TWC foundation was measured by use of a UV/VIS spectrophotometer type V-550 (JASCO, Japan) as follows.

6.0 mg of the TWC foundation was spread evenly by a finger on a 10 $cm^2$ tacky surface area of double faced tape attached on a transparent plastic sheet. The TWC foundation was covered with another transparent plastic sheet for sandwiching the powder sample. This test sheet was set in the V-550 sheet cell holder and the absorbance was measured from 260 nm to 400 nm. The averaged absorbance by the powder sample of 0.6 $mg/cm^2$ in the ranges of 260 nm to 320 nm and 320 nm to 400 nm were used for the values of the absorbance of UVB and UVA, respectively.

The results are shown in Tables 5 and 6. In Tables 5 and 6, [Mixture] means a TWC foundation including a mixture of the components shown in Tables 1 and 2 which has not yet been subjected to the hybridizer process, and [Composite Pigment] means a TWC foundation including a composite pigment obtained by the hybridizer process for the components shown in Tables 1 and 2.

TABLE 5

|  | UVB | | |
| --- | --- | --- | --- |
|  | [Mixture] | [Composite Pigment] | Ratio (%) |
| Ex. 1 | 1.00 | 1.13 | 113 |
| Ex. 2 | 1.48 | 1.53 | 104 |
| Ex. 3 | 1.22 | 1.56 | 129 |
| Ex. 4 | 1.53 | 1.58 | 103 |
| Ex. 5 | 0.98 | 0.96 | 99 |
| Comp. Ex. 1 | 1.00 | 1.02 | 103 |
| Comp. Ex. 2 | 1.14 | 1.16 | 103 |

Ratio(%): (UV absorbance [Composite Pigment])/(UV absorbance [Mixture])*100

TABLE 6

|  | UVA | | |
| --- | --- | --- | --- |
|  | [Mixture] | [Composite Pigment] | Ratio (%) |
| Ex. 1 | 0.71 | 0.83 | 116 |
| Ex. 2 | 0.90 | 1.08 | 119 |
| Ex. 3 | 0.69 | 0.96 | 138 |

TABLE 6-continued

| | UVA | | |
|---|---|---|---|
| | [Mixture] | [Composite Pigment] | Ratio (%) |
| Ex. 4 | 0.82 | 0.93 | 113 |
| Ex. 5 | 0.83 | 0.80 | 97 |
| Comp. Ex. 1 | 0.70 | 0.75 | 107 |
| Comp. Ex. 2 | 0.77 | 0.75 | 98 |

Ratio(%): (UV absorbance [Composite Pigment])/(UV absorbance [Mixture])*100

It is clear from Tables 5 and 6 that the cosmetics comprising the composite pigments of Examples 1 to 5 have better or equivalent UV filtering effects as compared to those comprising the composite pigments of Comparative Examples 1 and 2, and that the UV filtering effects of Examples 1 to 5 are generally enhanced, in particular in the UVA region, as compared to Comparative Examples 1 and 2.

In particular, Examples 1 to 4 which comprise a composite pigment including a combination of $TiO_2$ and Mexoryl show remarkable improvement in UV filtering effects in both UVA and UVB regions, in particular, in the UVA region. This can be attributed to the good dispersion of the UV filters on the core particle in the composite pigment used in Examples 1 to 4.

Examples 6-8

Example 1 was repeated to obtain a composite pigment for Examples 6 to 8 except that the components shown in Table 7 (the numerals in Table 7 are based on parts by weight) were used for Examples 6 to 8.

TABLE 7

| | Core | | | Shell | | |
|---|---|---|---|---|---|---|
| | NLK | Ca(b) | Ca(p) | $TiO_2$ | Red | Mexoryl |
| Ex. 6 | 100 | — | — | 4 | 10 | 4 |
| Ex. 7 | — | 100 | — | — | 10 | 4 |
| Ex. 8 | — | — | 100 | — | 10 | 4 |

NLK: A bowl-like particle of methylsilanol/silicate crosspolymer, NLK 506 marketed by Takemoto Oil & Fat Co., Ltd. in Japan
Ca(b): A particle of $CaCO_3$ in the form of a block, Omyapure 35 LM-OG, marketed by Omya in Australia
Ca(p): Petal type porous $CaCO_3$ marketed as LDR CA by New Lime Co., Ltd. and Toshiki Pigment Co., Ltd. in Japan
$TiO_2$: MT-100 TV marketed by Tayca Corporation in Japan
Red: Red 202
Mexoryl: Drometrizole trisiloxane Lipstick A lipstick was prepared by mixing a base, the components of which are shown in Table 8, with the composite pigment according to Examples 6 to 8 or the mixture of components shown in Table 7 Which has not yet been subjected to the hybridizer process such that the coloring pigment (Red 202) corresponds to 0.1 wt % of the lipstick, with a tricylinder roller at 90° C.

TABLE 8

| | Wt % |
|---|---|
| DIGLYCEROL ISOSTEARATE 3%, DIGLYCEROL DIISOSTEARATE 90%, DIGLYCEROL TRIISOSTEARATE 5%, ISOSTEARIC ACID 2% ISOSTEARIC ACID 2% | 19.05 |
| DI-MERATE DE DI-ISO-PROPYLE | 17.65 |
| HYDROGENATED POLYISOBUTENE | 14.29 |
| ISOPARAFFINE (6-8 MOLES D'ISOBUTYLENE) HYDROGENEE | 13.93 |

TABLE 8-continued

| | Wt % |
|---|---|
| ESTERS D'ACIDES GRAS VEGETAUX, ISO-STEARIQUE, ADIPIQUE DE GLYCERYLE | 11.91 |
| PURE JOJOBA OIL | 11.19 |
| LIPEX 102 SHEA BUTTER | 7.14 |
| VP/HEXADECENE COPOLYMER | 4.77 |
| DITERTIOBUTYL 4-HYDROXYTOLUENE | 0.07 |
| Total | 100 |

[Color Determination]

Color (L*,a*,b*) of each of the lipsticks according to Examples 6 to 8 was measured by using a DATACOLOR 600 (Applied Color Systems Inc., US) as follows.

2.5 g of the lipstick was poured into an aluminum pan (25 mm(L)*23 mm(W)*4 mm(D)) and cooled to solidify the paste. The L*, a* and b* of the test sample were measured from the top of the paste.

The results are shown in Tables 9-11. In Tables 9-11, [Mixture] means a lipstick including a mixture of the components shown in Table 7 which has not yet been subjected to the hybridizer process, and [Composite Pigment] means a lipstick including a composite pigment obtained by the hybridizer process for the components shown in Table 7.

TABLE 9

| | L* | |
|---|---|---|
| | [Mixture] | [Composite Pigment] |
| Ex. 6 | 43.31 | 43.31 |
| Ex. 7 | 41.51 | 43.54 |
| Ex. 8 | 41.28 | 42.93 |

TABLE 10

| | *a | |
|---|---|---|
| | [Mixture] | [Composite Pigment] |
| Ex. 6 | 45.97 | 50.96 |
| Ex. 7 | 44.06 | 51.58 |
| Ex. 8 | 43.71 | 49.76 |

TABLE 11

| | b* | |
|---|---|---|
| | [Mixture] | [Composite Pigment] |
| Ex. 6 | 13.38 | 19.11 |
| Ex. 7 | 15.06 | 22.42 |
| Ex. 8 | 14.42 | 20.49 |

It is clear from Tables 9-11 that the cosmetics comprising the composite pigments of Examples 6 to 8 have higher a* and b* values as compared to those comprising a simple mixture of components corresponding to the composite pigment.

Accordingly, cosmetics comprising the composite pigment according to the present invention can provide a better color with higher chroma compared to conventional cosmetics comprising a simple mixture of components corresponding to the composite pigment.

The invention claimed is:

1. A composite pigment, comprising:
   a substrate; and
   a layer comprising a solid organic UV filter,
   wherein a surface of the substrate is at least partially covered by the layer, and the layer is obtained by a mechanochemical fusion process.

2. The composite pigment of claim 1, wherein the layer further comprises a solid inorganic UV filter.

3. The composite pigment of claim 1, wherein the layer further comprises a second UV filter.

4. The composite pigment of claim 1, wherein the layer further comprises a coloring pigment.

5. The composite pigment of claim 1, wherein the substrate has a mean diameter in a range from 0.1 µm to 30 µm.

6. The composite pigment of claim 1, wherein the layer has a thickness in a range of 0.03 µm to 10 µm.

7. The composite pigment of claim 1, wherein the substrate comprises at least one selected from the group consisting of an inorganic material and a organic material.

8. The composite pigment of claim 7, wherein the inorganic material is at least one selected from the group consisting of mica, synthetic mica, talc, sericite, boron nitride, glass flake, calcium carbonate, barium sulfate, titanium oxide, hydroxyapatite, silica, silicate, zinc oxide, magnesium sulfate, magnesium carbonate, magnesium trisilicate, aluminum oxide aluminum silicate, calcium silicate, calcium phosphate, magnesium oxide, bismuth oxychloride, kaolin, hydrotalcite, mineral clay, synthetic clay, and iron oxide.

9. The composite of claim 7, wherein the organic material is at least one selected from the group consisting of a poly(meth)acrylate, a polyamide, a silicone, a polyurethane, a polyethylene, a polypropylene, a polystyrene, a polyhydroxyalkanoate, a polycaprolactam, a poly(butylenes) succinate, a polysaccharide, a polypeptice, a polyvinyl alcohol, a polyvinyl resin, a fluoropolymer, a wax, an amidosulfonic acid polyvalent metal salt, and an acylated amino acid.

10. The composite pigment of claim 1, wherein the solid organic UV filter is selected from the group consisting of a benzotriazole derivative, an oxanilide derivative, a triazine derivative, a triazole derivative, a vinyl-group comprising an amide, a cinnamic acid amide, and a sulfonated benzimidazole.

11. The composite pigment of claim 2, wherein the solid inorganic UV filter is at least one selected from the group consisting of silicone carbide, optionally coated metal oxides, and mixtures thereof.

12. The composite pigment of claim 3, wherein the second UV filter is at least one selected from the group consisting of an anthranilic derivative; a dibenzoylmethane derivative; a liquid cinnamic derivative; a salicyclic derivative; a camphor derivative; a benzophenone derivative; a β,β-diphenylacrylate derivative; a liquid triazine derivative; a liquid benzotriazole derivative; a benzalmalonate derivative; a benzimidazole derivative; an imidazoline derivative; a bis-benzoazolyl derivative; p-aminobenzoic acid (PABA) and a derivative thereof; a methylenebis(hydroxyphenylbenzotriazole) derivative; a benzoxazole derivative; a screening polymer and a screening silicone; a dimer derived from α-alkylstyrene; a 4,4-diarylbutadiene; octocrylene and a derivative thereof; guaiazulene and a derivative thereof; rutin and a derivative thereof; a flavonoid; a biflavonoid; oryzanol and a derivative thereof; quinic acid and a derivative thereof; a phenol; retinol; cysteine; an aromatic amino acid; and a peptide comprising an aromatic amino acid residue.

13. The composite pigment of claim 4, wherein the coloring pigment is at least one selected from the group consisting of titanium dioxide, zirconium ozide, cerium oxide, zinc oxides, an iron oxide, chromium oxide, manganese violet, ultramarine blue, chromium hydrate, ferric blue, aluminum powder, copper powder, carbon black, a pigment of D&C type, a lake, and a pearlescent pigment.

14. The composite pigment of claim 1, wherein a weight ratio of the substrate to the solid organic UV filter is from 100:1 to 100:500.

15. A method for preparing the composite pigment of claim 1, the method comprising;
   mechanochemical fusing a substrate, a solid organic UV filter, and optionally, at least one selected from the group consisting of a solid inorganic UV filter, a second UV filter, and a coloring pigment, to form the composite pigment.

16. A cosmetic composition, comprising a composite pigment of claim 1.

17. A cosmetic composition, comprising a composite pigment obtained by the method of claim 15.

18. The composite pigment of claim 1, wherein at least 50% of the substrate surface is covered by the layer.

19. The composite pigment of claim 1, wherein at least 80% of the substrate surface is covered by the layer.

20. The composite of claim 8, wherein the organic material is selected from the group consisting of a poly(meth)acrylate, a polyamide, a silicone, a polyurethane, a polyethylene, a polypropylene, a polystyrene, a polyhydroxyalkanoate, a polycaprolactam, a poly(butylenes) succinate, a polysaccharide, a polypeptide, a polyvinyl alcohol, a polyvinyl resin, a fluoropolymer, a wax, an amidosulfonic acid polyvalent metal salt, and an acylated amino acid.

\* \* \* \* \*